(12) United States Patent
Kang et al.

(10) Patent No.: US 10,539,573 B2
(45) Date of Patent: Jan. 21, 2020

(54) BIOMARKER FOR DIAGNOSING VASCULAR DISEASES AND THE USES THEREOF

(71) Applicant: Wonmedical Corp., Gyeonggi-do (KR)

(72) Inventors: Sang Won Kang, Seoul (KR); Dong Hoon Kang, Gyeonggi-do (KR)

(73) Assignee: WONMEDICAL CORP., Gyeonggi-Do (KR)

(*) Notice: Subject to any disclaimer, the term of this patent is extended or adjusted under 35 U.S.C. 154(b) by 6 days.

(21) Appl. No.: 15/673,618

(22) Filed: Aug. 10, 2017

(65) Prior Publication Data
US 2017/0363640 A1 Dec. 21, 2017

Related U.S. Application Data

(63) Continuation-in-part of application No. PCT/KR2016/001301, filed on Feb. 5, 2016.

(51) Int. Cl.
| | | |
|---|---|---|
| G01N 33/68 | (2006.01) | |
| C07K 16/28 | (2006.01) | |
| G01N 33/50 | (2006.01) | |

(52) U.S. Cl.
CPC ..... *G01N 33/6869* (2013.01); *C07K 16/2866* (2013.01); *G01N 33/5023* (2013.01); *G01N 33/5061* (2013.01); *G01N 33/6842* (2013.01); *G01N 2333/5434* (2013.01); *G01N 2500/10* (2013.01); *G01N 2570/00* (2013.01); *G01N 2800/32* (2013.01)

(58) Field of Classification Search
None
See application file for complete search history.

(56) References Cited

U.S. PATENT DOCUMENTS

2014/0302536 A1  10/2014  Snider et al.

FOREIGN PATENT DOCUMENTS

| CN | 1942201 A | 4/2007 |
|---|---|---|
| CN | 102176919 A | 9/2011 |
| JP | 2014-510707 A1 | 5/2014 |
| KR | 10-2010-0126445 A | 12/2010 |
| WO | 2005/079837 A1 | 9/2005 |
| WO | 2010/021756 A1 | 2/2010 |
| WO | WO 2013/134286 A2 | 9/2013 |

OTHER PUBLICATIONS

Krohn et al, the Journal of Physiology, 2016; vol. 594, No. 11; pp. 2895-2903.*
Sun et al, European Review for Medical and Pharmacological Sciences; 2017; vol. 21, pp. 5197-5206.*
Kishore et al, Journal of Cardiovascular Translational Research; 2016; vol. 9, pp. 169-175.*
Notice of Allowance corresponding to Korean Patent Application No. 10-2015-0020481, dated Jun. 21, 2018, pp. 4.
Extended European Search Report corresponding to European Patent Application No. 16749430.1, dated Jul. 4, 2018, 8 pages.
First Office Action corresponding to Japanese Patent Application No. 2017-542865, dated Sep. 5, 2018, pp. 4.
Office Action corresponding to Chinese Patent Application No. 201680001261.2, dated Sep. 28, 2017—provided with an English translation, 29 pgs.
Gyorgy et al. (2011) "Membrance vesicles, current state-of-the-art: emerging role of extracellular vesicles," Cell. Mol. Life Sci. 68:2667-2688.
Office Action corresponding to Korean Patent Application No. 10-2015-0020481, dated Oct. 23, 2017—Search results at the bottom of p. 5 only.
Apple et al. (2005) "Future biomarkers for detection of ischemia and risk stratification in acute coronary syndrome," Clinical Chemistry. 51(5):810-824.
Levula et al. (2012) "Genes involved in systemic and arterial bed dependent atherosclerosis—Tampere Vascular Study," PloS one. 7(4):e33787.
Xavier et al. (2012) "Association study of IL10 and IL23R-IL12RB2 in Iranian patients with Behcet's disease," Arthritis & Rheumatology. 64(8):2761-2772.
Zhang et al. (2003) "Induction of experimental autoimmune encephalomyelitis in IL-12 receptor-β2-deficient mice: IL-12 responsiveness is not required in the pathogenesis of inflammatory demyelination in the central nervous system," The Journal of Immunology. 170(4):2153-2160.
International Search Report corresponding to International Patent Application No. PCT/KR2016/001301, dated Jun. 1, 2016.

* cited by examiner

*Primary Examiner* — Bridget E Bunner
*Assistant Examiner* — Fozia Hamud
(74) *Attorney, Agent, or Firm* — Lathrop Gage LLP; Michael J. Spellberg; Andrew T. Wilkins

(57) ABSTRACT

Provided are a composition for diagnosing vascular disease including an agent measuring a level of interleukin 12 receptor β2 protein in the blood, and a kit for diagnosing vascular disease including the same. Further, provided is a method for diagnosing vascular disease, the method including the step of measuring a level of interleukin 12 receptor β2 protein in a blood sample separated from an individual suspected of having vascular disease. Furthermore, provided are a composition for preventing or treating vascular disease including an interleukin 12 receptor β2 activity inhibitor, and a method of screening a therapeutic agent for vascular disease, the method including the step of treating smooth muscle cells with a test agent for vascular disease treatment and measuring an expression level of interleukin 12 receptor β2.

5 Claims, 13 Drawing Sheets
Specification includes a Sequence Listing.

*P<0.02

BIOMARKER FOR DIAGNOSING VASCULAR DISEASES AND THE USES THEREOF

RELATED APPLICATIONS

This Application is a Continuation-in-part of Application PCT/KR2016/001301 filed on Feb. 5, 2016. Application PCT/KR2016/001301 claims priority to Korean Application 10-2015-0020481, filed on Feb. 10, 2015 in the Republic of Korea. The entire contents of these applications are incorporated herein by reference in their entirety.

SEQUENCE LISTING

This application contains a Sequence Listing in computer readable format. The Sequence Listing is provided as a file entitled 593819_HNT-044BUSCIP_Sequence_Listing.txt created Aug. 17, 2017 which is 16,539 bytes in size. The information in the computer readable format of the Sequence Listing is incorporated herein by reference in its entirety.

TECHNICAL FIELD

The present invention relates to a composition for diagnosing vascular disease including an agent measuring a level of interleukin 12 receptor β2 protein in the blood, and a kit for diagnosing vascular disease including the same. Further, the present invention relates to a method for diagnosing vascular disease, the method including the step of collecting or isolating an extracellular vesicle derived from smooth muscle cells in a blood sample separated from an individual suspected of having vascular disease and the step of measuring a level of interleukin 12 receptor β2 protein in the collected or isolated extracellular vesicle. Furthermore, the present invention relates to a composition for preventing or treating vascular disease including an interleukin 12 receptor β2 activity inhibitor, and a method of screening a therapeutic agent for vascular disease, the method including the step of treating smooth muscle cells with a test agent for vascular disease treatment and measuring an expression level of interleukin 12 receptor β2.

BACKGROUND OF THE INVENTION

Atherosclerosis is the primary cause of coronary artery disease and cerebrovascular disease, both diseases underlies about 50% of all deaths in westernized countries. The early lesions of atherosclerosis include sub-endothelial accumulations of lipid-engorged macrophages (foam cells), which are represented as "fatty streak" lesions. Fatty streaks are not clinically harmful, but they can be the precursors of more advanced fibrous and plaque-type lesions characterized by the accumulation of lipid-rich necrotic debris and smooth muscle cells (SMCs).

During the disease progression, the arterial wall gradually thickens and hardens to form an atherosclerotic plaque, resulting in the narrowing of the arterial lumen. When such intimal thickening of artery blood vessel further develops the narrowing of the arterial lumen and the plaques become fragile, unstable angina is accompanied. Subsequently, they abruptly rupture and cause ischemic symptoms or a blood clot, and often myocardial infarction or heart attack. However, since intimal thickening due to atherosclerosis progresses for many decades without marked subjective symptoms, the intimal thickening cannot easily be diagnosed before the appearance of ischemic symptoms.

When a stenotic lesion by intimal thickening is found, the vascular intervention by angioplasty including stent or percutaneous coronary angioplasty is generally performed to eliminate the luminal narrowing and to widen the vessel. However, such angioplasty procedure results in endothelial denudation, and subsequently, and intimal thickening of blood vessel due to hyperproliferation of vascular smooth muscle cells leads to restenosis. Accordingly, there is an urgent need to develop a method for rapid and easy non-invasive diagnosis of intimal thickening of blood vessel in the related field.

Until now, many attempts have been undertaken to identify the early diagnostic biomarkers for atherosclerosis in human-derived samples and model animals. The clinical data from a follow-up study of 3,209 participants in the Framingham Heart Study for more than 7 years revealed several valuable biomarkers [C-reactive protein, B-type natriuretic peptide (BNP), renin, urinary albumin, and homocysteine]. Serum proteomics and metabolomics experiments have also been aggressively conducted for many years to search for circulating biomarkers that show a correlation with the progression of the disease. Nonetheless, there have been no clinically applicable biomarkers, in particular, plasma-derived biomarkers owing to the problems of the inter-individual variability and inaccessibility of human tissues with vascular thickening.

SUMMARY OF THE INVENTION

Under this background, the present inventors adapted a differential proteomics strategy using the balloon-injured carotid vessels of genetically congenic rats and filtered out the proteins irrelevant to the smooth muscle cell hyperplasia by an in vitro validation using human aortic smooth muscle cells (HASMCs). Consequently, they identified candidate proteins via in vitro and in vivo validation, most of which are functionally novel in relation to the neointimal SMC hyperplasia. As a result, they found that the plasma occurrence of interleukin 12 receptor β2 protein shows a correlation to the severity of clinical manifestations resulted from plaque instability, and interleukin 12 receptor β2 protein in the blood can be used as a biomarker for vascular disease, thereby completing the present invention.

An object of the present invention is to provide a composition for diagnosing vascular disease, the composition including an agent measuring a level of interleukin 12 receptor β2 protein in the blood.

Another object of the present invention is to provide a kit for diagnosing vascular disease, the kit including an antibody or an aptamer specifically binding to a smooth muscle cell marker and an agent measuring a level of interleukin 12 receptor β2 protein.

Still another object of the present invention is to provide a method for diagnosing vascular disease, the method including the step of collecting or isolating an extracellular vesicle derived from smooth muscle cells in a blood sample separated from an individual suspected of having vascular disease and the step of measuring a level of interleukin 12 receptor β2 protein in the collected or isolated extracellular vesicle.

Still another object of the present invention is to provide a composition for preventing or treating vascular disease, the composition including an interleukin 12 receptor β2 activity inhibitor.

Still another object of the present invention is to provide a method of screening a therapeutic agent for vascular disease, the method including the steps of treating smooth muscle cells with a test agent for vascular disease treatment and measuring an expression level of interleukin 12 receptor β2.

According to the present invention, when interleukin 12 receptor β2 is used as a biomarker for vascular disease, in particular, myocardial infarction, acute coronary syndrome, or unstable angina, vascular disease, of which diagnosis has been performed only by angiography, can be diagnosed using blood in a rapid non-invasive economic manner. Accordingly, the early diagnosis of vascular disease is possible, since the disease has been diagnosed based on subjective symptoms after the appearance of ischemic symptoms with development of the disease. The promise of early diagnosis, prevention and treatment is realized.

BRIEF DESCRIPTION OF DRAWINGS

FIG. 7C shows the result of Western blot analysis of plasma samples obtained from a normal group and patients with unstable angina using IL-1212β2 protein, in which equal amounts of protein loading are ensured by Pon S staining and the arrowhead indicates the position of IL-1212β2 protein;

DETAILED DESCRIPTION OF THE INVENTION

Figure 1:
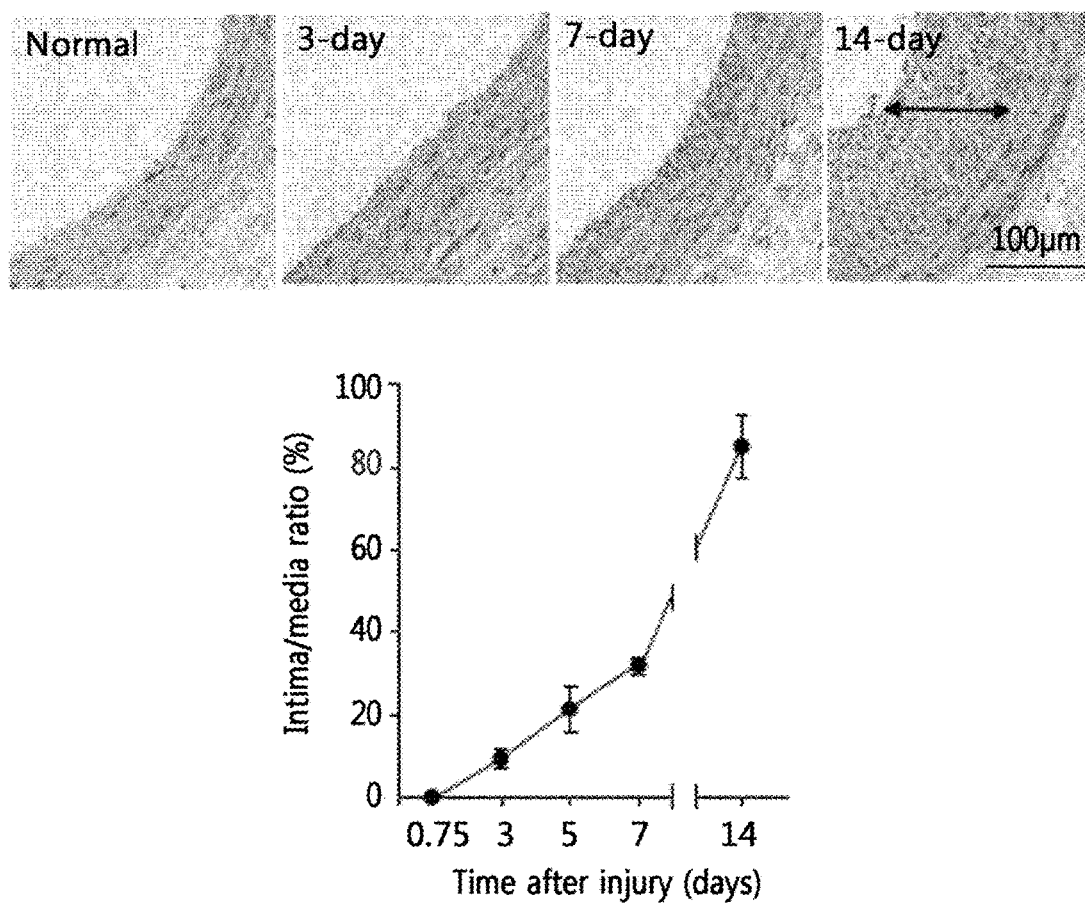
FIG. 1 is the result of neointimal tissue staining showing the kinetics of neointimal thickening during recovery time in balloon-injured carotid artery.

In an aspect to achieve the above objects, the present invention provides a composition for diagnosing vascular disease, the composition including an agent measuring a level of interleukin 12 receptor β2 protein in the blood.

When an endothelium, which is an intima making contact with blood flow, is damaged by a vascular disease, it causes smooth muscles, i.e., media, to make contact with blood flow. As a result, a smooth muscle-derived extracellular vesicle, which is not present in bloods of a healthy individual, exists in those of an individual having vascular disease, and the smooth muscle-derived extracellular vesicle overexpresses interleukin receptor β2 protein. Accordingly, the present invention is based on the discovery that vascular disease can be diagnosed by i) collecting or isolating an extracellular vesicle derived from smooth muscles in a blood sample from an individual; and ii) measuring a level of interleukin receptor β2 protein in the extracellular vesicle.

As used herein, the term "vascular disease" refers to a disease which involves damage to the blood vessel tissues and present symptoms of neointimal thickening therefrom, without limitation. As for the vascular disease of the present invention, progression of the neointimal thickening may cause stenosis and decrease of elasticity of vassel wall, leading to hemorrhage by vascular rupture. In the present invention, vascular disease may be intimal thickening, unstable angina, myocardial infarction (such as acute myocardial infarction), atherosclerosis, acute coronary syndrome, or in-stent restenosis, but is not limited thereto.

In the present invention, it is confirmed that interleukin 12 receptor β2 in the blood is a biomarker for vascular damage and thickening, and it may be used for the diagnosis of a disease group with the risk of heart attack, such as unstable angina, myocardial infarction (acute myocardial infarction), etc. Therefore, the level of interleukin 12 receptor β2 protein in the blood may be measured, that is, the composition for predicting or diagnosing vascular disease of the present invention may be used to achieve the early diagnosis of the risk of heart attack.

As used herein, the term "interleukin 12 receptor β2 (IL-12Rβ2)" refers to a subunit β2 of a receptor protein binding to interleukin 12 ligand. It is known that the corresponding protein is involved in the JAK2/STAT4 pathway, and functions to promote proliferation of T cell and NK cell, in particular, differentiation of T cell to Th1 cell. Information about this gene or protein may be available in the known database, and exemplified by NCBI GenBank, but is not limited thereto. In the present invention, the interleukin 12 receptor β2 protein may be a full-length human interleukin 12 receptor β2 protein, and have an amino acid sequence of SEQ ID NO: 1.

The composition for diagnosing vascular disease of the present invention may include an antibody or aptamer specific to interleukin 12 receptor β2 protein. In the present invention, the antibody specific to interleukin 12 receptor β2 protein may be particularly Santa Cruz Biotech. Clone E-20, Catalog # sc-18648 and/or Atlas antibodies. Product # HPA024168

In a specific embodiment of the present invention, Santa Cruz Biotech. Clone E-20, Catalog # sc-18648 and/or Atlas antibodies. Product # HPA024168 were/was used as the antibody specific to interleukin 12 receptor β2 protein, thereby measuring the level of interleukin 12 receptor β2 protein.

On the other hand, the composition for diagnosing vascular disease of the present invention may be used to measure the blood level of interleukin 12 receptor β2 protein which is derived from smooth muscle cells of vascular endothelium.

The interleukin 12 receptor β2 protein corresponds to a subunit of the receptor protein binding to interleukin 12 ligand. In particular, the interleukin 12 receptor β2 protein is a transmembrane protein which is generally found in the cell membrane, and there have been no reports about the presence of the corresponding protein in the blood. In the present invention, the present inventors demonstrated for the first time that the level of interleukin 12 receptor β2 protein can be measured in the blood and the interleukin 12 receptor β2 protein shows a correlation with vascular disease, for example, unstable angina, myocardial infarction, acute coronary syndrome, etc.

In the present invention, the interleukin 12 receptor β2 protein found in the blood may be derived from cells of vascular endothelium which are damaged by vascular thickening, namely, smooth muscle cells (SMCs). In other words, interleukin 12 receptor β2 protein is overexpressed in damaged vascular endothelium by vascular thickening, and the membrane protein, interleukin 12 receptor β2 protein may be present in extracellular vesicles (exosomes, etc.) derived from the damaged tissue. The extracellular vesicles may exist in the blood, and therefore, the blood level of the interleukin 12 receptor β2 protein may be measured.

The composition for diagnosing vascular disease of the present invention includes an agent measuring the level of interleukin 12 receptor β2 protein which shows a differential level in a blood sample of an individual having vascular disease, for example, myocardial infarction, acute coronary syndrome, or unstable angina, compared to a blood sample of a normal control group, and therefore, the composition may be used to diagnose vascular disease of the individual. That is, when the level of interleukin 12 receptor β2 protein in the blood of the individual, which is measured by the composition of the present invention, is higher than the level of interleukin 12 receptor β2 protein in the blood of the normal control group, the corresponding individual may be diagnosed to have vascular disease.

Figure 7A:
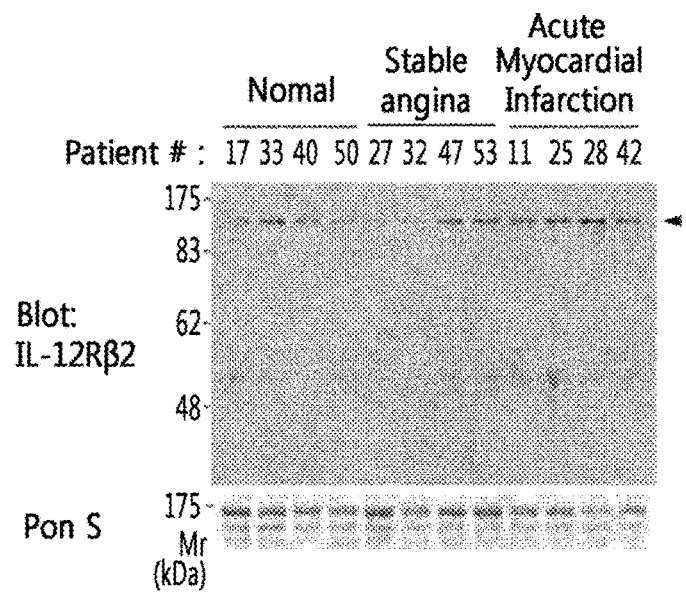
FIG. 7A, FIG. 7B, and FIG. 7C show the results of Western blot analysis of plasma samples obtained from a normal group and patients with stable angina or acute myocardial infarction using IL-1212β2 protein (FIG. 7A), and the result of Western blot analysis of plasma samples obtained from a normal group and patients with stable angina or acute myocardial infarction using IL-1212β2 protein (FIG. 7B)
Figure 7B:
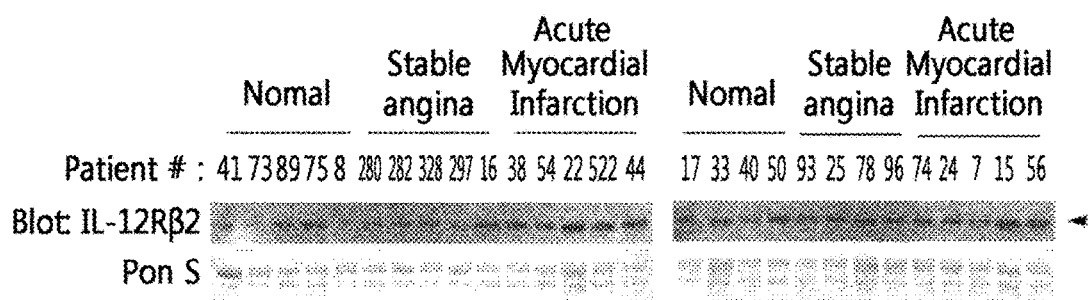
Figure 7C:
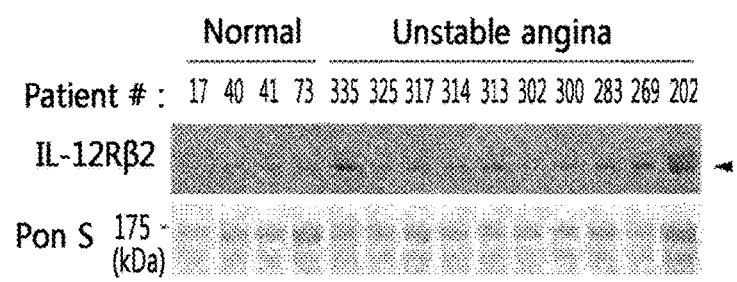
Figure 8A:
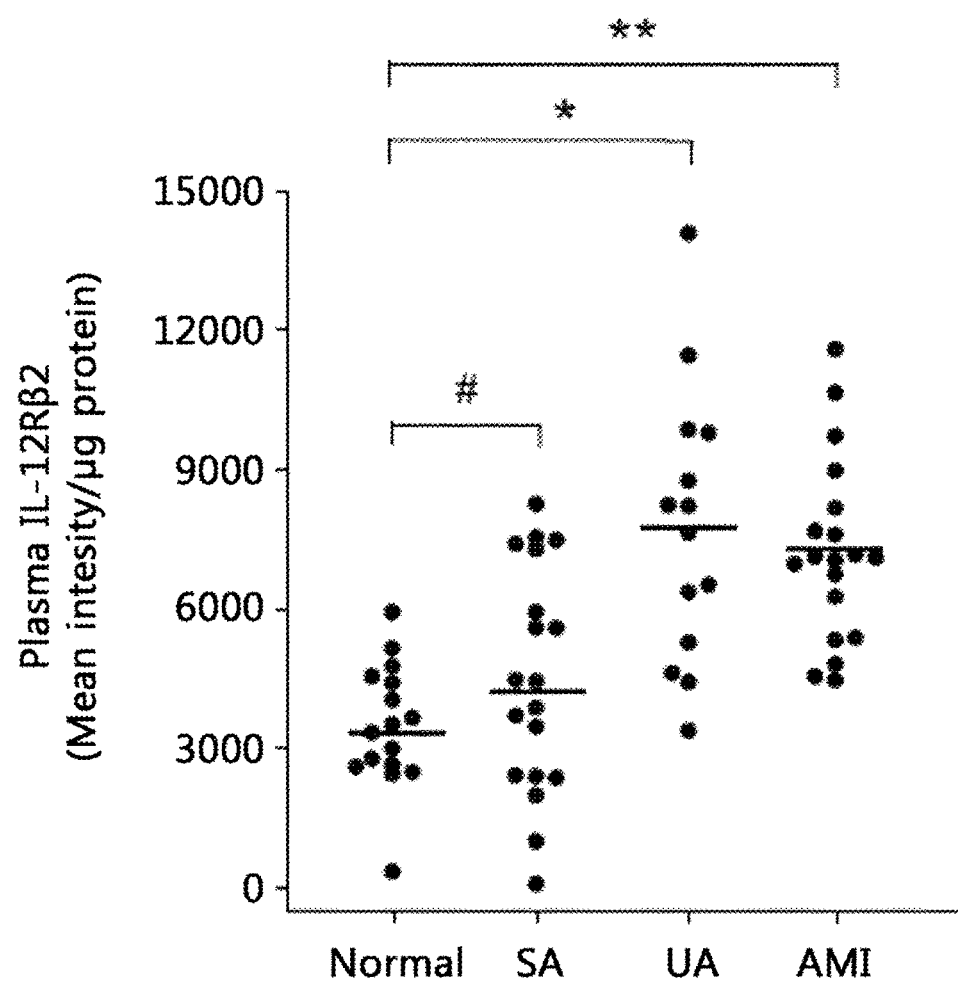
FIG. 8A is a graph showing quantification and statistic analysis of IL-1212β2 protein bands of FIG. 7A, FIG. 7B, and FIG. 7C, the bands indicating IL-1212β2 protein expression levels in plasma samples obtained from as normal group and patients with stable angina (SA), unstable angina (UA), or acute myocardial infarction (AMI)

In a specific embodiment of the present invention, the levels of interleukin 12 receptor β2 protein were measured in blood samples of a normal control group, a stable angina patient group at the low risk of intimal thickening or heart attack, an unstable angina patient group, and a myocardial infarction patient group. As a result, remarkably high levels of IL-1212β2 protein were observed in the samples of patients groups, compared to the sample of the normal group (FIGS. 7 and 8a).

In the present invention, the composition for measuring the level of interleukin 12 receptor β2 protein derived from smooth muscle cells may include i) an antibody or aptamer specific to interleukin 12 receptor β2 protein as an agent measuring the level of interleukin 12 receptor β2 protein; and ii) an antibody or aptamer specifically binding to a smooth muscle marker. The composition of the present invention may further include iii) an antibody or aptamer specifically binding to an extracellular vesicle marker, in addition to i) and ii).

Specifically, the smooth muscle marker may be a platelet-derived growth factor receptor (PDGFR), but is not limited thereto.

In an embodiment of the present invention, to measure the blood level of interleukin 12 receptor β2 protein derived from smooth muscle cells of vascular endothelium, extracellular vesicles containing the smooth muscle cell marker are first separated from the blood using the antibody or aptamer specifically binding to the corresponding markers, and then the level of interleukin 12 receptor β2 protein may be measured in the extracellular vesicles.

Figure 9A:
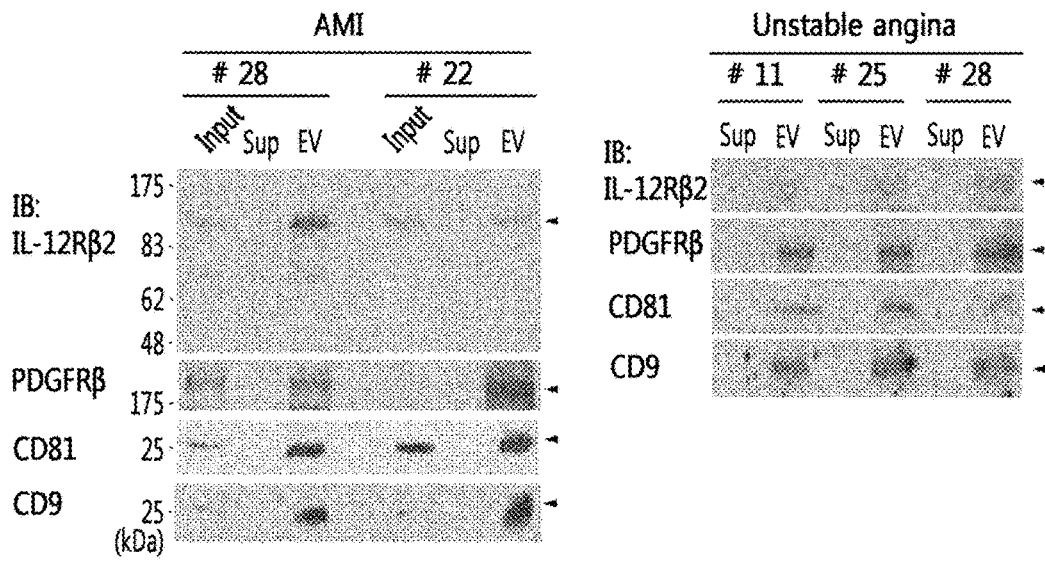
FIG. 9A shows the result of Western blot analysis of IL-1212β2 and CD9 and CD81 as extracellular vesicle markers in extracellular vesicle fractions isolated by ultracentrifugation of the plasma samples obtained from patients with acute myocardial infarction and unstable angina.
Figure 9B:
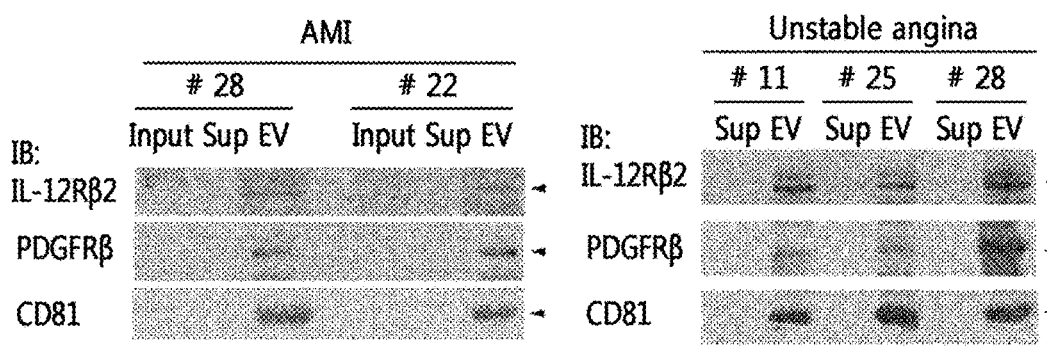
FIG. 9B shows the result of Western blot analysis of IL-1212β2, CD81 as an extracellular vesicle marker, and PDGFRβ as a smooth muscle marker in extracellular vesicle fractions isolated by polymer-based precipitation of the plasma samples obtained from patients with acute myocardial infarction and unstable angina.
Figure 9C:
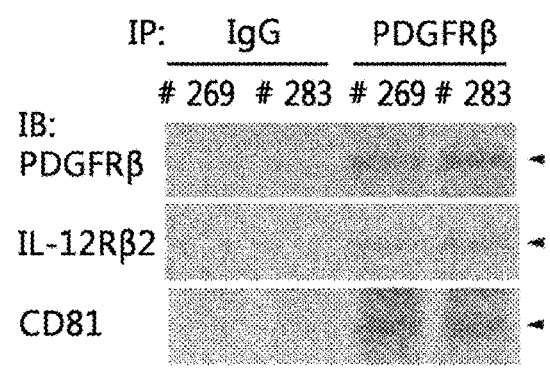
FIG. 9C shows the result of Western blot analysis of IL-1212β2 in immunoprecipitates obtained by immunoprecipitation of PDGFRβ in the plasma samples obtained from patients with acute myocardial infarction and unstable angina.

In a specific embodiment of the present invention, an antibody (Santa Cruz Biotech. clone P-20. Catalog # sc-339) specifically binding to a smooth muscle marker, PDGFR was used to separate an extracellular vesicle, and then the level of interleukin 12 receptor β2 protein was measured in the separated extracellular vesicle (FIG. 9C).

In the present invention, the measuring the blood level of interleukin 12 receptor β2 protein is to measure the level of interleukin 12 receptor β2 protein in extracellular vesicles present in the blood, and the extracellular vesicle may be especially exo some, but is not limited thereto.

To this end, the composition of the present invention may include an antibody or aptamer specific to an extracellular vesicle marker, and the extracellular vesicle marker may be CD81, CD9 or CD63. The antibody specific to the extracellular vesicle marker may be an antibody (System Biosciences Inc. Cat # EXOAB-CD63A-1) specifically binding to CD63, an antibody (System Biosciences Inc. Cat# EXOAB-CD9A-1) specifically binding to CD9, and/or an antibody (System Biosciences Inc. Cat# EXOAB-CD81A-1) specifically binding to CD81. With respect to the objects of the present invention, the extracellular vesicle, for example, exosomes, etc. in which the level of interleukin 12 receptor β2 protein is measured, may be derived from blood vessels, in particular, damaged endothelium. In a specific embodiment of the present invention, as the antibody specific to the extracellular vesicle marker, an antibody (System Biosciences Inc. Cat # EXOAB-CD63A-1) specifically binding to CD63, an antibody (System Biosciences Inc. Cat# EXOAB-CD9A-1) specifically binding to CD9, and/or an antibody (System Biosciences Inc. Cat# EXOAB-CD81A-1) specifically binding to CD81 were/was used.

As used herein, the term "marker" refers to a substance capable of diagnosing vascular disease by distinguishing an individual having vascular disease, in particular, myocardial infarction, acute coronary syndrome, or unstable angina from a normal individual or an individual at low risk of heart attack, and the marker includes all organic biological molecules, quantities of which are increased or decreased in an individual having vascular disease of the present invention, such as polypeptides, proteins or nucleic acids, lipid, glycolipids, glycoproteins, sugars, etc. In the present invention, the marker may be specifically a protein which is increased in an individual having vascular disease of the present invention, but is not limited thereto.

As used herein, the "measuring the protein level" is a process of assessing the presence and expression level of the marker protein in a biological sample (e.g., whole blood, plasma, serum, a fraction thereof, etc.) in order to diagnose the vascular disease of the present invention. In particular, an antibody or aptamer specifically binding to the protein may be used to examine the amount of the protein. The biological sample may be a biological sample separated from an individual.

Analysis methods therefor may include, but are not limited to, Western blotting, enzyme linked immunosorbent assay (ELISA), radioimmunoassay (RIA), radioimmunodiffusion, ouchterlony immunodiffusion, rocket immunoelectrophoresis, immunohistostaining, immunoprecipitation assay, complement fixation assay, fluorescence activated cell sorter (FACS), an aptamer chip, a microarray, a protein chip, etc. With the analysis methods, the amount of antigen-antibody complex formed in a patient suspected of having vascular disease may be compared to that in a normal control group, thereby diagnosing whether vascular disease actually occurs in the patient suspected of having vascular disease.

As used herein, the term "antibody" refers to a specific protein molecule that indicates an antigenic region. With respect to the objects of the present invention, the antibody may be an antibody specifically binding to a marker protein, and includes all of polyclonal antibodies, monoclonal antibodies, recombinant antibodies, and antigen-binding fragments thereof, as long as they retain an antigen-binding function. Furthermore, the antibody of the present invention includes specialized antibodies, such as humanized antibodies, etc.

Production of the antibody specific to interleukin 12 receptor β2 protein, which is a marker protein for vascular disease of the present invention, in particular, myocardial infarction, acute coronary syndrome, or unstable angina, may be easily carried out using techniques widely known in the art. Polyclonal antibodies may be produced by a method widely known in the art, which includes injecting the interleukin 12 receptor β2 protein antigen (full length or fragment) into an animal and collecting blood samples from the animal to obtain serum containing antibodies. Such polyclonal antibodies may be prepared from a certain animal host, such as goats, rabbits, sheep, monkeys, horses, pigs, cows and dogs. Monoclonal antibodies may be prepared by a method widely known in the art, such as a hybridoma method (see hybridoma method)(Kohler and Milstein (1976) European Journal of Immunology 6:511-519), or a phage antibody library technique (Clackson et al, Nature, 352:624-628, 1991; Marks et al, J. Mol. Biol., 222:58, 1-597, 1991). Antibodies prepared by the above methods may be separated and purified using gel electrophoresis, dialysis, salting out, ion exchange chromatography, affinity chromatography or the like.

Further, the antibodies of the present invention include not only complete forms having two full-length light chains and two full-length heavy chains, but also functional fragments of antibody molecules. The functional fragments of antibody molecules refer to fragments retaining at least an antigen-binding function, and include Fab, F(ab'), F(ab")$_2$, Fv and the like.

As used herein, the term "aptamer" refers to a single stranded oligonucleotide of about 20~60 nucleotides and a nucleic acid molecule with binding activity to a specific target molecule. Aptamers have diverse tertiary structures according to their sequences and high affinity to a particular substance, like in an antigen-antibody reaction. By binding to a specific target molecule, the aptamer may detect the target molecule or inhibit its activity. The aptamer of the present invention may be RNA, DNA, modified nucleic acid or a mixture thereof, and it may be in linear chain or angular shape. Preferably, the aptamer may bind to interleukin 12 receptor β2 to detect interleukin 12 receptor β2 or to inhibit its activity. The aptamer may be prepared from the sequence of interleukin 12 receptor β2 by those skilled in the art using a known method.

Meanwhile, as used herein, the term "antigen-antibody (or aptamer) complex" refers to a binding product of the interleukin 12 receptor β2 protein and an antibody or aptamer specific thereto. The amount of formed antigen-antibody complex may be quantitatively determined by measuring the signal size of a detection label.

Such a detection label may be selected from the group consisting of enzymes, fluorescent substances, ligands, luminescent substances, microparticles, redox molecules and radioactive isotopes, but is not limited thereto. Examples of enzymes available as detection labels include, but are not limited to, β-glucuronidase, β-D-glucosidase, β-D-galactosidase, urase, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, β-latamase, etc. Examples of the fluorescent substances include, but are not limited to, FITC, RITC, fluorescin, isothiocyanate, rhodamine, phycoerythrin, phycocyanin, allophycocyanin, o-phthaldehyde, fluorescamine, etc. Examples of the ligands include, but are not limited to, biotin derivatives, etc. Examples of luminescent substances include, but are not limited to, acridinium esters, luciferin, luciferase, etc. Examples of the microparticles include, but are not limited to, colloidal gold, colored latex, etc. Examples of the redox molecules include, but are not limited to, ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$ and $[MO(CN)_8]^{4-}$, etc. Examples of the radioactive isotopes include, but are not limited to, $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$, etc.

Preferably, the protein expression levels are measured by ELISA. ELISA include a variety of ELISA methods, including direct ELISA using a labeled antibody or aptamer recognizing an antigen immobilized on a solid support, indirect ELISA using a labeled antibody recognizing a capture antibody or aptamer forming complexes with an antigen immobilized on a solid support, direct sandwich ELISA using another labeled antibody recognizing an antigen in an antigen or aptamer-antibody complex immobilized on a solid support, and indirect sandwich ELISA, in which another labeled antibody recognizing an antigen in an antigen-antibody or aptamer complex immobilized on a solid support is reacted, and then a labeled secondary antibody recognizing the another labeled antibody is used.

As used herein, the term "diagnosis" refers to evaluation of the presence or properties of pathological states. With respect to the objects of the present invention, the diagnosis is to determine the incidence of vascular disease, in particular, myocardial infarction, acute coronary syndrome, or unstable angina, progression of the disease, and risk of heart attack caused thereby.

In another aspect, the present invention provides a kit for diagnosing vascular disease, the kit including the composition for diagnosing vascular disease of the present invention. Specifically, the kit may comprise an antibody or an aptamer specifically binding to a smooth muscle cell marker and an agent measuring a level of interleukin 12 receptor β2 protein.

The kit of the present invention may be used to determine the level of interleukin 12 receptor β2 protein as a marker for vascular disease, in particular, myocardial infarction, acute coronary syndrome, or unstable angina, thereby detecting the marker. The kit for detecting the marker of the present invention may be selected from the group consisting of a microarray, an aptamer chip kit, an ELISA (enzyme linked immunosorbent assay) kit, a blotting kit, an immunoprecipitation kit, an immunofluorescence assay kit, a protein chip kit, and a combination thereof, which are able to detect interleukin 12 receptor β2 protein.

The kit for detecting the marker of the present invention may include an aptamer or antibody for detecting interleukin 12 receptor β2 protein and determining the level of interleukin 12 receptor β2 protein.

In another specific embodiment, the kit for determining the level of interleukin 12 receptor β2 protein in the present invention may include a substrate for immunological detection of the aptamer or antibody, an appropriate buffer, an antibody or aptamer labeled with a detection label, and/or a color development substrate. As the substrate, a nitrocellulose membrane, a 96-well plate made of polyvinyl resin, a 96-well plate made of polystyrene resin, and a glass slide may be used. The detection label is the same as described above. As the substrate agent for color development, any substrate, such as ABTS (2,2'-azino-bis(3-ethylbenzothiazoline-6-sulfonic acid)), OPD (o-phenylenediamine), or TMB (tetramethyl benzidine), which is apparent to those skilled in the art, may be used depending on the detection label.

In still another aspect, the present invention provides a method for diagnosing vascular disease, the method including the steps of collecting or isolating an extracellular vesicle derived from smooth muscle cells in a blood sample separated from an individual suspected of having vascular disease and measuring a level of interleukin 12 receptor β2 protein in the extracellular vesicle collected or isolated.

Specifically, the present invention provides a method for diagnosing vascular disease, the method including the steps of (a) collecting or isolating an extracellular vesicle derived from smooth muscle cells in a blood sample separated from an individual suspected of having vascular disease; (b) measuring a level of interleukin 12 receptor β2 protein in the extracellular vesicle collected or isolated through step (a); and (c) comparing the level of interleukin 12 receptor β2 protein measured in step (b) with that in a sample of a normal control group.

In the present invention, the vascular disease, diagnosis, interleukin 12 receptor β2, etc. are the same as described above.

Further, the method for diagnosing vascular disease according to the present invention may further comprises measuring a level of the extracellular vesicle derived from smooth muscle cells obtained from step (a) using an antibody or an aptamer specific to a extracellular vesicle marker. Then, the extracellular vesicle marker may be CD81, CD9, or CD63, but is not limited thereto.

For example, prior to measuring the level of interleukin 12 receptor β2 protein, vascular disease may preliminarily be diagnosed by measuring the level of the extracellular vesicle derived from smooth muscles cells, obtained from step (a). Specifically, as stated above, in consideration of smooth muscles making contact with blood flow when blood vessels are damaged, it can be suspected that vascular disease is developed when it is confirmed through the steps above that the extracellular vesicle derived from smooth muscle cells exists in the blood sample.

In the present invention, the blood sample refers to a blood sample (e.g., whole blood, plasma, serum, a fraction thereof, etc.) collected to diagnose vascular disease in an individual suspected of having vascular disease, in particular, it may be a plasma sample or an extracellular vesicle fraction, but is not limited thereto. In the present invention, the extracellular vesicle may be exosome, but is not limited thereto.

In the method for diagnosing vascular disease according to the present invention, step (a) of collecting or isolating the extracellular vesicle derived from smooth muscle cells in a blood sample may be performed using an antibody or aptamer specifically binding to a smooth muscle marker, but is not limited thereto.

The method of providing information for diagnosing vascular disease of the present invention can be characterized in that when the level of interleukin 12 receptor β2 protein measured in the blood sample separated from an individual suspected of having vascular disease is higher than that in the sample of the normal control group, the individual is diagnosed to have vascular disease.

In the method of providing information for diagnosing vascular disease of the present invention, the measuring the level of interleukin 12 receptor β2 protein in the blood sample separated from an individual suspected of having vascular disease may be measuring the level of interleukin 12 receptor β2 protein derived from cells of vascular endothelium, namely, smooth muscle cells present in the blood sample, and the measuring may be performed by separating or extracting extracellular vesicles (e.g., exosomes) derived from cells of vascular endothelium, namely, smooth muscle cells in the blood sample, and then measuring the level of interleukin 12 receptor β2 protein present therein.

In an embodiment of the present invention, in order to measure the level of interleukin 12 receptor β2 protein derived from smooth muscle cells of vascular endothelium in the blood, extracellular vesicles containing the smooth muscle marker are first separated from the blood using an antibody or aptamer specifically binding to the corresponding marker, and then the level of interleukin 12 receptor β2 protein may be measured in the corresponding extracellular vesicles.

In a specific embodiment of the present invention, an antibody specifically binding to a smooth muscle marker, PDGFRβ was used, and the level of interleukin 12 receptor β2 protein was measured in extracellular vesicles which are separated using the antibody (FIG. 9C).

In still another aspect, the present invention provides a composition for preventing or treating vascular disease, the composition including an interleukin 12 receptor β2 activity inhibitor.

In the present invention, the vascular disease, interleukin 12 receptor β2, etc. are the same as described above.

As used herein, the term "interleukin 12 receptor β2 activity inhibitor" refers to any agent capable of reducing the expression or activity of interleukin 12 receptor β2, and specifically, it may include all agents capable of reducing the expression level or activity of interleukin 12 receptor β2 by reducing the expression of interleukin 12 receptor β2 at a transcriptional level or interrupting its activity.

The interleukin 12 receptor β2 activity inhibitor may be a compound, a nucleic acid, a peptide, a virus or a vector containing the nucleic acid, which targets interleukin 12 receptor β2 to inhibit the expression or activity of interleukin 12 receptor β2, and there is no limitation in the form. The interleukin 12 receptor β2 activity inhibitor may be, but is not limited to, preferably, an oligonucleotide inhibiting interleukin 12 receptor β2 mRNA expression, an antibody inhibiting the activity of interleukin 12 receptor β2 protein, or an antigen-binding fragment thereof. In particular, the oligonucleotide inhibiting interleukin 12 receptor β2 mRNA expression may be antisense oligonucleotide, aptamer or siRNA specific to interleukin 12 receptor β2. That is, the interleukin 12 receptor β2 activity inhibitor in the present invention may be selected from the group consisting of anti-interleukin 12 receptor β2 protein antibody, and antisense oligonucleotide, aptamer, siRNA, shRNA and microRNA specific to interleukin 12 receptor β2 gene. The siRNA specific to interleukin 12 receptor β2 gene may be prepared by a method known in the art with reference to the base sequence of interleukin 12 receptor (32.

In a specific embodiment of the present invention, 4 types of siRNAs specific to interleukin 12 receptor β2 gene were treated to carotid artery balloon injury models, resulted in the significant reduction in neointimal thickening.

As used herein, the term "antisense oligonucleotide" refers to DNA, RNA or its derivative which contains a nucleic acid sequence complementary to the sequence of a particular mRNA, and the antisense oligonucleotide functions to inhibit translation of mRNA into a protein by binding to the complementary sequence in mRNA. The antisense oligonucleotide sequence means a DNA or RNA sequence which is complementary to and binds to interleukin 12 receptor β2 mRNA, and is able to inhibit translation, translocation into cytoplasm, maturation, or other essential activities for overall biological functions. The antisense oligonucleotide may be 6 to 100 bases in length, preferably 8 to 60 bases in length, and more preferably 10 to 40 bases in length. The antisense oligonucleotide may be either synthesized in vitro and administered into the body or it may be synthesized in vivo. An example of synthesizing the antisense oligonucleotide in vitro is to use RNA polymerase I. An example of synthesizing the antisense RNA in vivo is to use a vector having the origin of the multiple cloning site (MCS) in opposite direction so that the antisense RNA is transcribed. Preferably, the antisense RNA may have a translation stop codon within its sequence in order to prevent translation into a peptide sequence.

Design of the antisense oligonucleotide to be used in the present invention may be readily performed according to a method known in the art with reference to the base sequence of interleukin 12 receptor β2.

As used herein, the term "siRNA" refers to a nucleotide molecule capable of mediating RNA interference or gene silencing. Since siRNA can suppress the expression of the target gene, it provides an effective way of gene knockdown or genetic therapy. The siRNA is a small RNA fragment in the size of 21~25 nucleotides which is generated by cutting double-stranded RNA with a dicer. The siRNA specifically binds to mRNA having a complementary sequence thereto to suppress its expression. With respect to the objects of the present invention, the siRNA specifically acts on interleukin 12 receptor β2 to cleave interleukin 12 receptor β2 molecule, leading to induction of RNA interference (RNAi). Consequently, interleukin 12 receptor β2 may be suppressed. siRNA may be synthesized chemically or enzymatically. The preparation method of siRNA is not particularly limited, and any method known in the art may be used. For example, the method may include direct chemical synthesis of siRNA, synthesis of siRNA by in vitro transcription, enzymatic cleavage of long double-stranded RNA synthesized by in vitro transcription, expression by transferring an shRNA-expressing plasmid or viral vector to cells, and expression by transferring PCR (polymerase chain reaction)-derived siRNA expression cassette to cells, but is not limited thereto.

In a specific embodiment of the present invention, Cat # M_007932-00 specifically suppressing human interleukin 12 receptor β2 and Cat # M_095069-01 specifically suppressing rat interleukin 12 receptor β2 (manufactured by GE Dharmacon) were used to examine the effects.

As used herein, the term "treatment" refers to clinical intervention in an attempt to alter the natural course of the individual or cell being treated, and may be performed either for prophylaxis or during the course of clinical pathology. Desirable therapeutic effects include preventing occurrence or recurrence of disease, alleviation of symptoms, and diminishment of any direct or indirect pathological consequences of the disease, preventing metastasis, lowering the rate of disease progression, amelioration or palliation of the disease state, and remission or improved prognosis. In the present invention, the treatment preferably means all of the actions in which the symptoms of vascular disease, in particular, vascular thickening, myocardial infarction, acute coronary syndrome, or unstable angina have been modified favorably by administration of the composition including the interleukin 12 receptor β2 inhibitor. Further, the "prevention" means all of the actions in which the occurrence of vascular disease, in particular, vascular thickening, myocardial infarction, acute coronary syndrome, or unstable angina is restrained or retarded by administration of the composition including the interleukin 12 receptor β2 inhibitor according to the present invention.

The pharmaceutical composition of the present invention may further include appropriate carriers, excipients, or diluents, generally used in preparation of a pharmaceutical composition. The composition including the pharmaceutically acceptable carrier may have various formulations for oral or parenteral administration. The formulation of the composition may involve using general diluents or excipients such as fillers, bulking agents, binders, wetting agents, disintegrants, surfactants, etc. The solid formulations for oral administration may include tablets, pills, powders, granules, capsules, etc. The solid formulations may be prepared by mixing one or more compounds with at least one excipient, for example, starch, calcium carbonate, sucrose, lactose, gelatin, etc. In addition to such simple excipients, lubricants such as magnesium stearate or talc may also be used. The liquid formulations for oral administration may include suspensions, solutions for internal use, emulsions, syrups, etc. In addition to general diluents such as water and liquid paraffin, different excipients may also be used, for example, wetting agents, flavors, fragrances, preserves, etc. The formulations for parenteral administration may include sterile aqueous solutions, non-aqueous solvents, suspensions, emulsions, lyophilized preparations, or suppositories. The non-aqueous solutions and the suspensions may include propylene glycol, polyethylene glycol, vegetable oil such as olive oil, injectable ester such as ethyloleate, etc. The base for suppositories may include witepsol, macrogol, tween 61, cacao butter, laurin butter, glycerogelatin, etc.

Further, the pharmaceutical composition of the present invention may have, but is not limited to, any one formulation selected from the group consisting of a tablet, a pill, a powder, a granule, a capsule, a suspension, a solution for internal use, an emulsion, a syrup, a sterile aqueous solution, a non-aqueous solvent, a suspension, an emulsion, a lyophilized preparation, and a suppository.

In still another aspect, the present invention provides a method of treating vascular disease, the method including the step of administering the pharmaceutical composition including the interleukin 12 receptor β2 inhibitor as an active ingredient to an individual.

As used herein, the term "individual" means all animals including humans who have a possibility of having vascular disease, in particular, vascular thickening, myocardial infarction, acute coronary syndrome, or unstable angina or have already had the disease. The vascular disease, in particular, vascular thickening, myocardial infarction, acute coronary syndrome, or unstable angina may be alleviated or treated by administering the pharmaceutical composition of the present invention to the individual. The alleviation means all of the actions in which vascular disease, in particular, vascular thickening, myocardial infarction, acute coronary syndrome, or unstable angina have taken a turn for the better or been modified favorably by administration of the composition according to the present invention.

The pharmaceutical composition of the present invention may be administered in a pharmaceutically effective amount.

As used herein, the term "administration" refers to introduction of the pharmaceutical composition of the present invention into a subject by a suitable route. As long as it allows the composition of the present invention to reach a target tissue, any oral or parenteral route may be used.

The pharmaceutical composition may be properly administered to an individual according to a method, an administration route, and an administration dose generally used in the art, depending on the purpose or necessity. The administration route may be exemplified by oral, parenteral, subcutaneous, intraperitoneal, intrapulmonary, topical, and intranasal administration. The parenteral administration may include topical (by use of stent), intramuscular, intravenous, intra-arterial, intraperitoneal, or subcutaneous administration. Further, a proper administration dose and frequency may be selected according to a method known in the art, and the dose and administration frequency of the pharmaceutical composition of the present invention practically administered may be properly determined by various factors such as the kind of symptoms to be treated, administration route, gender, health conditions, diet, an individual's age and body weight, and disease severity.

As used herein, the term "pharmaceutically effective amount" refers to an amount sufficient to inhibit or alleviate increase of vascular permeability, at a reasonable benefit/risk ratio applicable to any medical use. The effective dosage level may be determined depending on the kind of individual, severity, age, gender, drug activity, sensitivity to the drug, administration time, administration route and excretion rate, duration of treatment, drugs used simultaneously, and other factors known in the medical field. The composition of the present invention may be administered alone or in combination with other therapeutic agents, and may be administered sequentially or simultaneously with conventional therapeutic agents. The composition may be administered in a single or multiple dosage form. It is important to administer the composition in the minimum amount that can exhibit the maximum effect without causing side effects, in view of all the above-described factors, and it may be readily determined by those skilled in the art.

In still another aspect, the present invention provides a method of screening a therapeutic agent for vascular disease, the method including the steps of treating interleukin 12 receptor β2-expressing smooth muscle cells with a test agent for vascular disease treatment; and measuring an expression level of interleukin 12 receptor β2.

In detail, according to the screening method of the present invention, when the expression level of interleukin 12 receptor β2 is lowered by treatment of the test agent for vascular disease treatment, the test agent may be determined as a therapeutic agent for vascular disease.

The "test agent" includes any substance, molecule, element, compound, entity, or a combination thereof. The test agent includes, but is not limited to, e.g., a protein, a polypeptide, a small organic molecule, a polysaccharide, a polynucleotide, and the like. It may be a natural product, a synthetic compound, or a chemical compound, or a combination of two or more substances. Unless otherwise specified, the terms "agent", "substance", and "compound" may be used interchangeably.

Test agents that may be screened or identified by the method of the present invention include polypeptides, beta-turn mimetic s, polysaccharides, phospholipids, hormones, prostaglandins, steroids, aromatic compounds, heterocyclic compounds, benzodiazepines, oligomeric N-substituted glycines, oligocarbamates, saccharides, fatty acids, purines, pyrimidines, derivatives, structural analogs or combinations thereof. The test agent may be obtained from a wide variety of sources including libraries of synthetic or natural compounds.

EXAMPLES

Hereinafter, the present invention will be described in more detail with reference to Examples. However, these Examples are for illustrative purposes only, and the invention is not intended to be limited by these Examples.

Example 1: Preparation of Balloon-Induced Injury Model of Rat Carotid Artery

In the present invention, animal studies were performed in compliance with the guidelines of Institutional Animal Care and Use Committee (IACUC) of Ewha Womans University and conformed to "Guide for Care and Use of Laboratory Animals" published by the US National Institutes of Health (The National Academies Press, 8th Edition, 2011).

In the present invention, ten-week-old male Sprague-Dawley rats were used for a balloon-induced injury model of rat carotid artery, and the balloon-induced injury model of rat carotid artery was prepared as previously described (D H Kang, et al., Circulation 2013; 128:pp 834-844.). First, rats were anesthetized by inhalation of isoflurane gas ($N_2O:O_2$/70%:30%).

For proteomics analyses, the rats were recovered in the cages for different time points (18-hr, 3-day, 5-day, and 7-day) after a surgical operation. Each experimental group size was 8 rats and the sham operation was used for zero-time control.

For the histological and immunological analyses, the rats were recovered for 10 days. The group sizes in each experiment are described in the figure legends. All the animal experiments were repeated three times.

Example 2: Catheter-Mediated Intramural Delivery of siRNAs into Carotid Artery

In order to examine molecular biological changes by delivery of siRNA to injured carotid arteries of the carotid artery-injured animal model prepared in Example 1, catheter-mediated intramural delivery of siRNAs was performed.

In detail, the rat-specific siRNA SMART pools (GE Healthcare Dharmacon, Cat # M_095069-01, 200 nM) were premixed with siPORTTM NeoFXTM reagent following the manufacturer's instructions (Ambion). Immediately after the balloon injury, the common carotid arteries were washed with Opti-MEM and the transfection premix (200 µl) was administered through the catheter. The vessel was incubated for 15 minutes to allow the efficient transfection and then ligated. A fluorescent dye-conjugated control siRNA named siGLO-Red (Dharmacon) was used for confirming the intramural transfection of siRNA.

Example 3: Histological Analysis

For histological analysis, rats were anesthetized by inhalation of isoflurane gas ($N_2O:O_2$/70%:30%), as described in Example 1, and the common carotid arteries were excised after transcardiac perfusion-fixation with heparinized saline containing 3.7% formaldehyde. The excised carotid arteries were paraffin embedded and sectioned by rotary microtome (Leica RM2255). The two serial tissue sections (4 µm in thickness) were obtained from the middle area of common carotid arteries and stained with haematoxylin and eosin (H&E). The luminal, internal elastic laminal, and external elastic laminal areas were measured using NIH Image v1.62. The intimal and medial areas were determined by subtraction of the luminal area and the external elastic area from the internal elastic area. The values from two serial sections per rat were averaged for analysis.

Example 4: Analysis of Human Blood Specimen

Blood specimens used in the present invention were collected from normal healthy controls and patients with angiographically confirmed coronary artery disease, as approved by the institutional review board of Ewha Womans University Medical Center (Seoul, Korea).

Among the patients with coronary artery disease, those who had ischemic symptoms were classified as stable angina, unstable angina, and acute myocardial infarction according to clinical criteria. All volunteers participated in this study after agreeing their informed consent.

The collected whole blood samples were centrifuged, and the plasma samples were further clarified using Pierce albumin/IgG removal kit according to the manufacturer's protocol.

Example 5: Statistical Analysis

Data were analyzed with either Student's t-test for comparisons between two groups or one-way ANOVA with Tukey's 'honestly significant difference' post hoc test for multiple groups (SPSS 12.0K for Windows, SPSS, Chicago, Ill., USA) to determine the statistical significance (P value). A $P<0.05$ was considered to be statistically significant. Data using blood specimens were analyzed with two non-parametric tests: Kruskal-Wallis rank sum test and Wilcoxon rank sum test.

Experimental Example 1: Analysis of Proteome Change in Rat Carotid Vessels by a Physical Injury A balloon-induced injury of rat carotid artery involves the thrombosis-induced activation of SMC (smooth muscle cell) hyperplasia following endothelial denudation, which induces typical neointimal thickening and, therefore, resembles the physical injury of arterial vessels using a balloon embolectomy catheter. This in vivo model is sufficient for histological and biochemical studies related to the SMC hyperplasia.

Figure 2A:
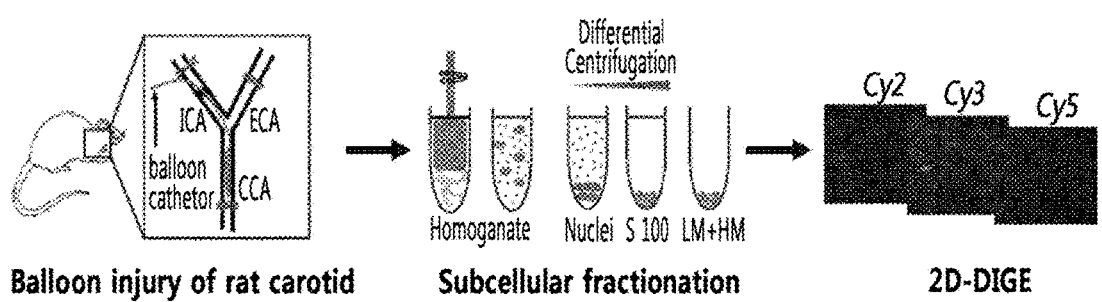
FIG. 2A illustrates an experimental procedure for proteomics analysis, in which a carotid artery balloon injury model was prepared, and proteins were extracted from the injured carotid artery, followed by 2-dimensional differential gel electrophoresis (2D-DIGE)

The kinetics of neointimal thickening in the balloon-injured carotid arteries was first examined. As previously reported, the balloon injury induced a gradual increase of neointimal thickness in the lumen side of injured lesion (FIG. 1). Based on this kinetics, the five serial time points (sham control and 18 hours, 3 days, 5 days and 7 days after injury) were chosen for the proteome analysis by two-dimensional differential gel electrophoresis (2D-DIGE) (FIG. 2A).

Figure 2B:
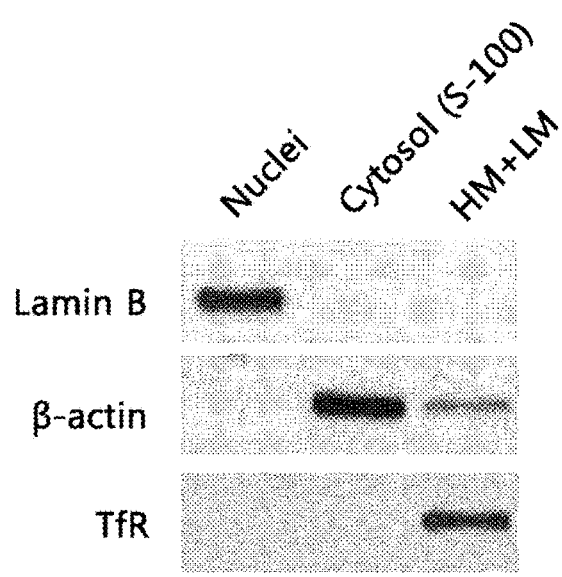
FIG. 2B is the result of analyzing subcellular fractionations obtained from injured carotid artery of the carotid artery balloon injury model by using markers.
Figure 2C:
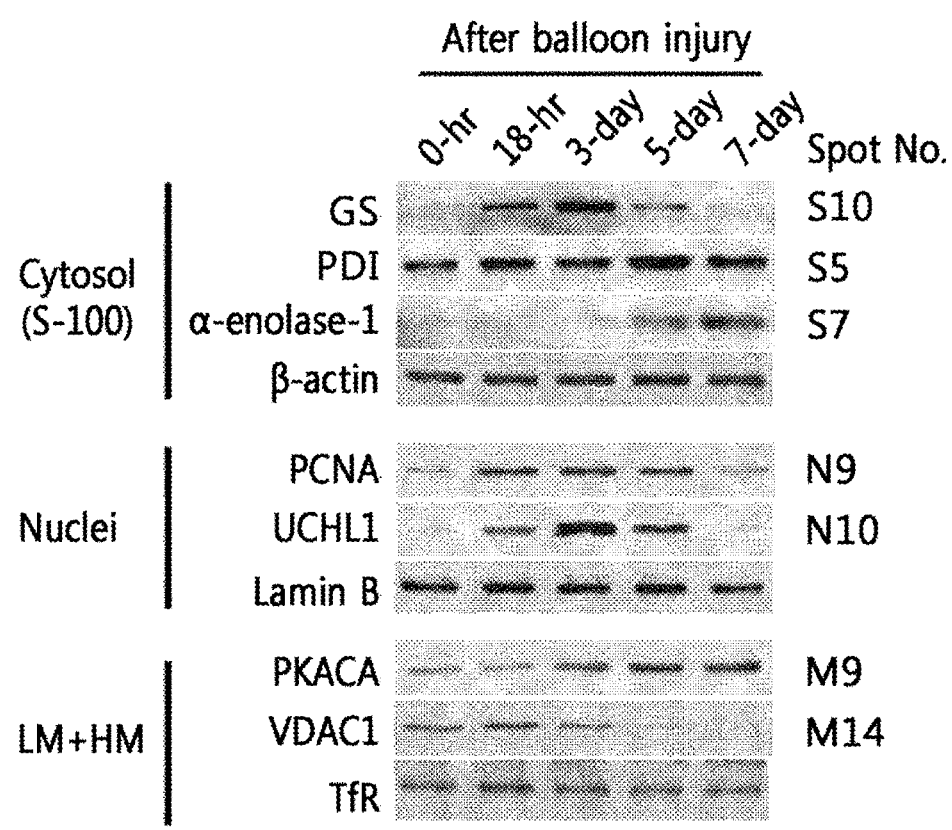
FIG. 2C shows the differential expressions of the identified proteins in the extraction solutions of the carotid arteries obtained during recovery time after injury, which were evaluated by Western blot analysis using their specific antibodies.
Figure 3A:
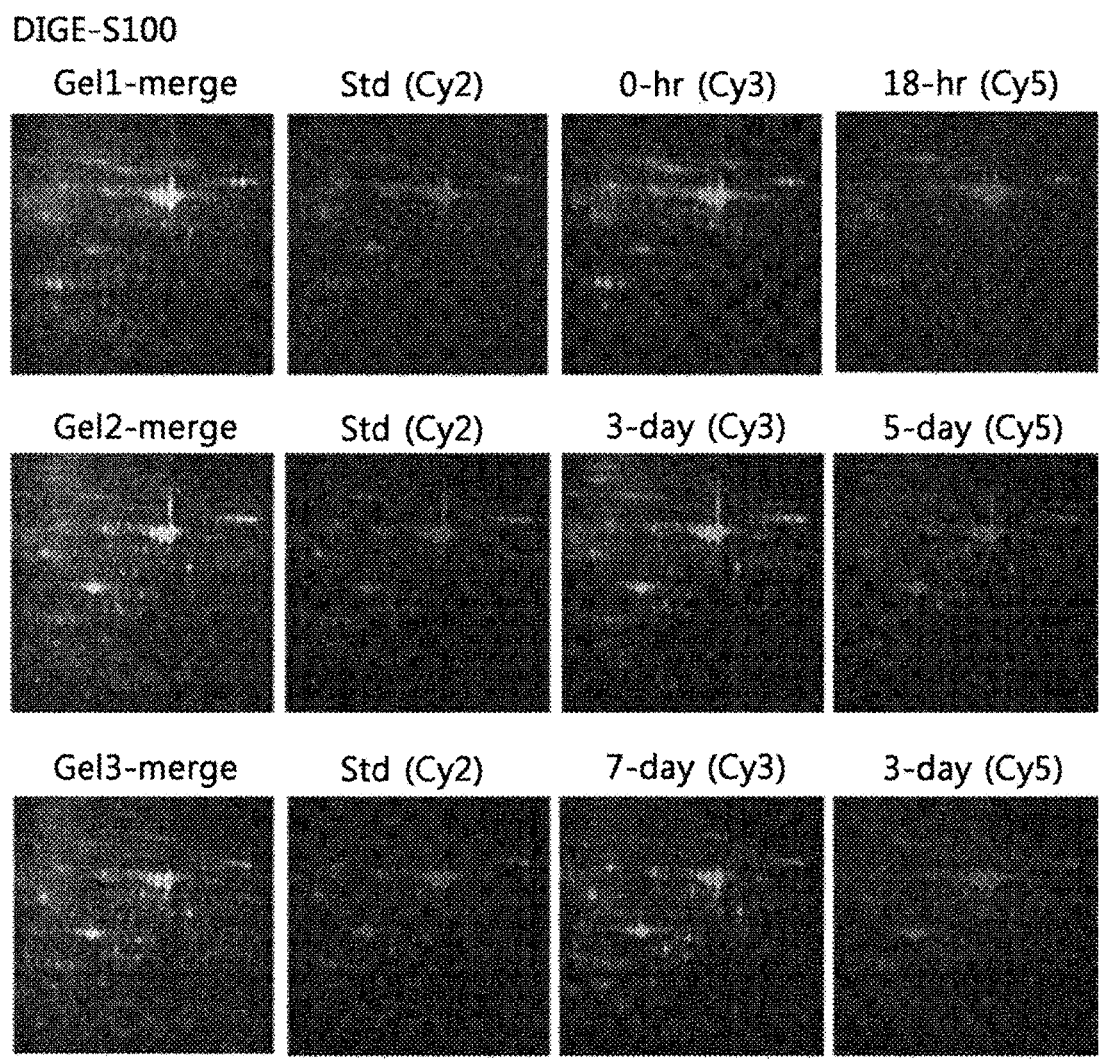
FIG. 3A shows representative fluorescence images of 2-dimensional differential gel electrophoresis (2D-DIGE) of cytosolic proteins (S-100 fractions) which were extracted from injured carotid arteries obtained after preparation of carotid artery balloon injury models.
Figure 3B:
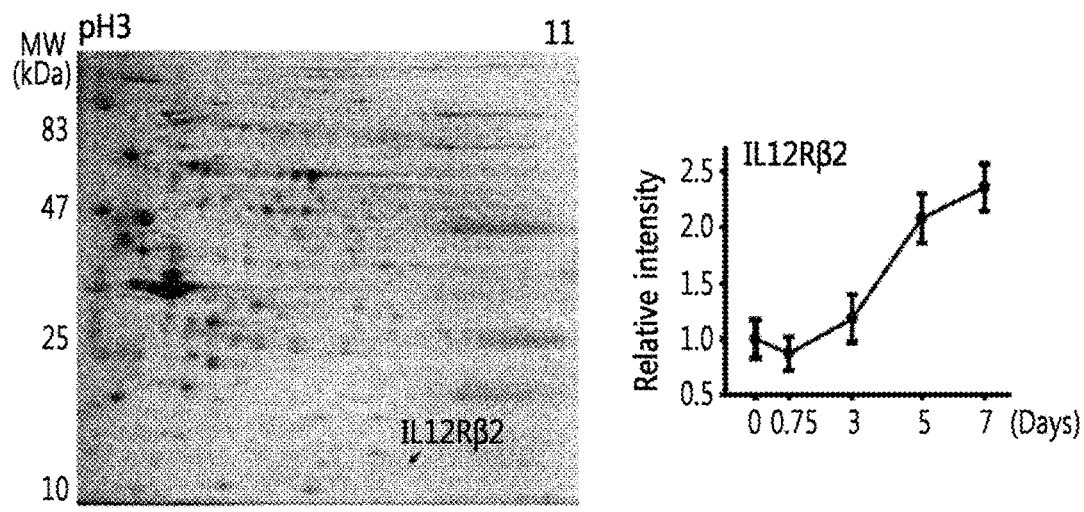
FIG. 3B shows the result of identifying interleukin 12 receptor β2 protein in the protein spots obtained from proteomics analysis by 2-dimensional differential gel electrophoresis (2D-DIGE) of the proteins which were extracted from injured carotid arteries obtained after preparation of carotid artery balloon injury models, in which the graph shows increased expression of interleukin 12 receptor β2 protein quantified by fluorescence image analysis, over recovery time after injury.

To obtain sufficient amount of proteins for DIGE analysis, protein extraction from total 8 injured carotid fragments collected at each time point was performed and subcellular fractionation was performed for separation (FIG. 2B). The protein fractions were stained with Cy3/Cy5 fluorescence, followed by two-dimensional differential gel electrophoresis, and the expression of more than 2,100 protein spots was analyzed. By plotting the protein expression at each injured sample versus internal standard (Cy2-labeled), it was found that about 140 protein spots showed the expression change in a time-dependent manner. Among the 140 proteins, 44 proteins were successfully identified by mass spectrometry. The differential expression of the identified proteins was confirmed by immunoblotting with specific antibodies ((IL-1212β2-specific antibody; Santa Cruz Biotech. Clone E-20, Catalog # sc-18648/Atlas antibodies. Product # HPA024168)), thus supporting that the proteome analyses were quantitative and accurate (FIG. 2C).

Experimental Example 2: In Vitro and In Vivo Assays for Validating Function of Interleukin 12 Receptor β2

Focusing on the change of interleukin 12 receptor β2 among 44 proteins identified in Experimental Example 1, its cellular function was validated in human aortic smooth muscle cells (HASMCs).

In detail, the expression of IL-1212β2 (interleukin 12 receptor (32) was knocked down in human aortic smooth muscle cells by treatment with a mixture of four IL-1212β2-specific small interfering RNAs (siRNAs) (GE Healthcare Dharmacon, Cat # M_007932-00). Since platelet-derived growth factor (PDGF) and TNF-α are the major factors produced by platelets/macrophages in the balloon-injured lesions, the proliferation and chemotactic migration of aortic smooth muscle cells were induced by PDGF-BB and the monocyte adhesion to smooth muscle cells was induced by tumor necrosis factor-α (TNF-α).

Figure 4:
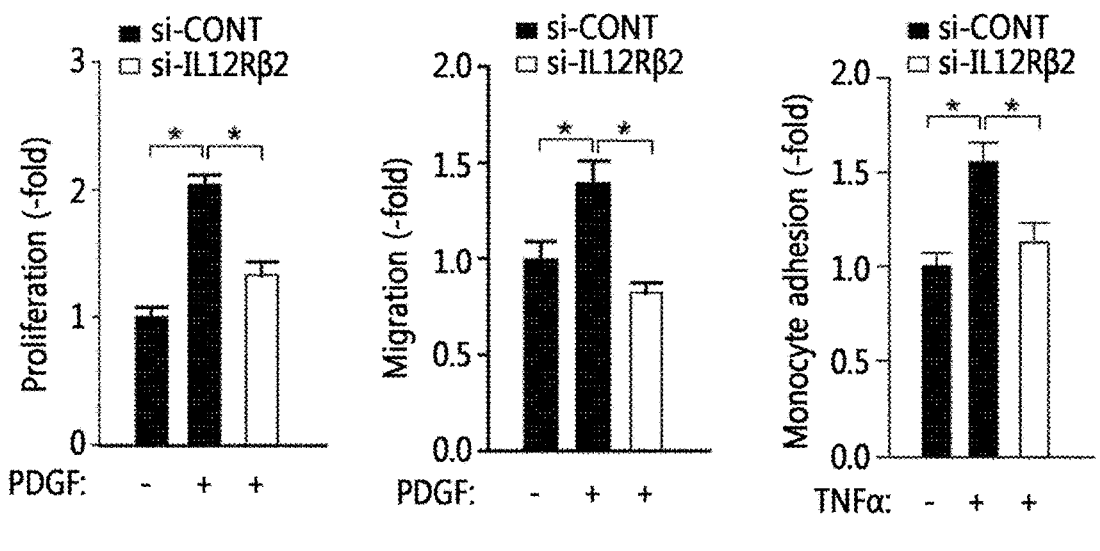
FIG. 4 shows the effect of IL-1212β2 knockdown on three activities of SMC cells (proliferation and chemotactic migration of human aortic smooth muscle cells and monocyte adhesion to smooth muscle cells)

As a result, the knockdown of interleukin 12 receptor β2 significantly reduced three types of cell activities (FIG. 4).

Figure 5A:
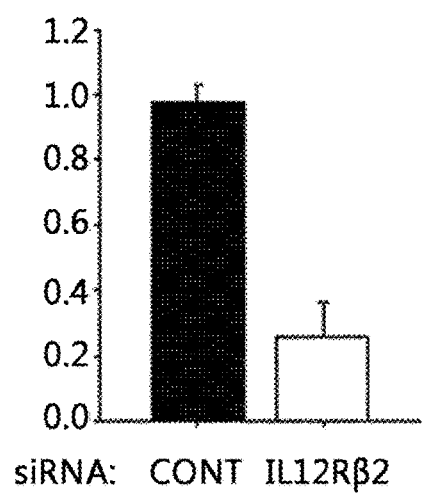
FIG. 5A and FIG. 5B show comparisons of the IL-1212β2 expression level after delivery of IL-1212β2 siRNA to balloon-injured carotid artery (FIG. 5A), and the result of H&E tissue staining to analyze thickness of neointimal tissue (FIG. 5B)
Figure 5B:
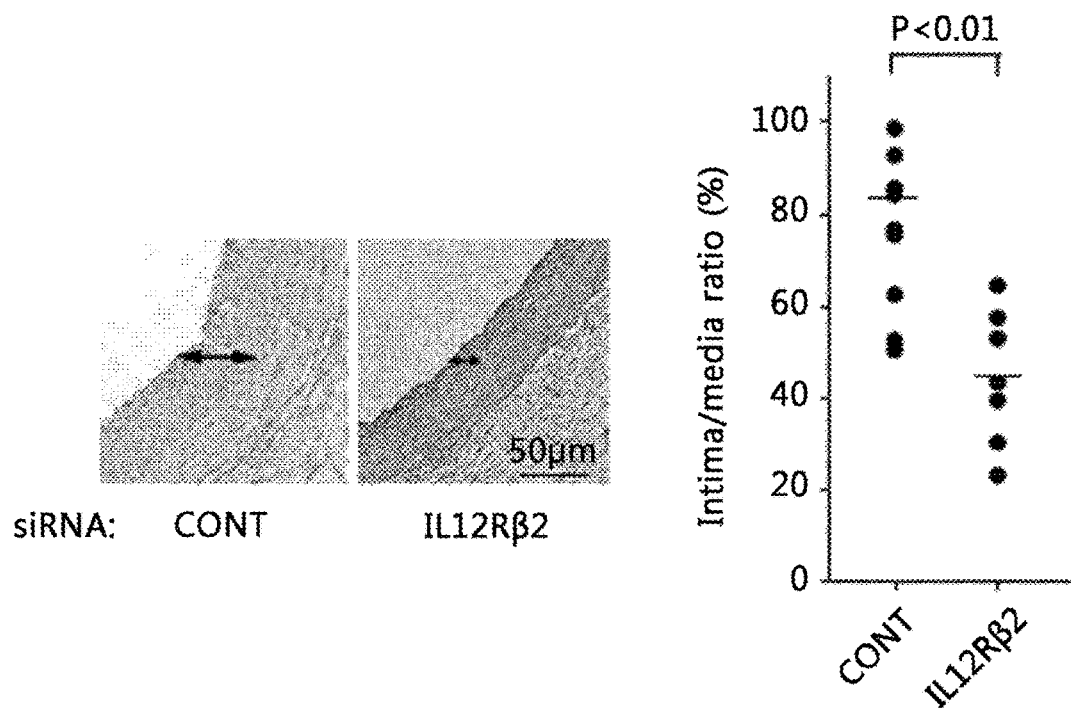

Further, when catheter-mediated transfection of rat-specific IL-1212β2 (interleukin 12 receptor β2) siRNA to the balloon-injured carotid arteries was performed as described in Example 2, the knockdown of IL-1212β2 was successfully established (FIG. 5A), and neointimal thickening was remarkably reduced, compared to a control siRNA (FIG. 5B), indicating that IL-1212β2 is expressed in vascular smooth muscle cells and involved in smooth muscle cell hyperplasia.

Experimental Example 3: IL-12Rβ2 as Potential Biomarker for Vascular Thickening 1

Because rapidly growing or damaged cells release the cellular proteins or micro RNAs in the form of extracellular vesicles, for example, exosomes etc., the present inventors assessed that IL-1212β2 protein with high expression can appear in the blood of patients with coronary artery disease, especially patients with unstable symptoms such as acute myocardial infarction or unstable angina.

Figure 6A:
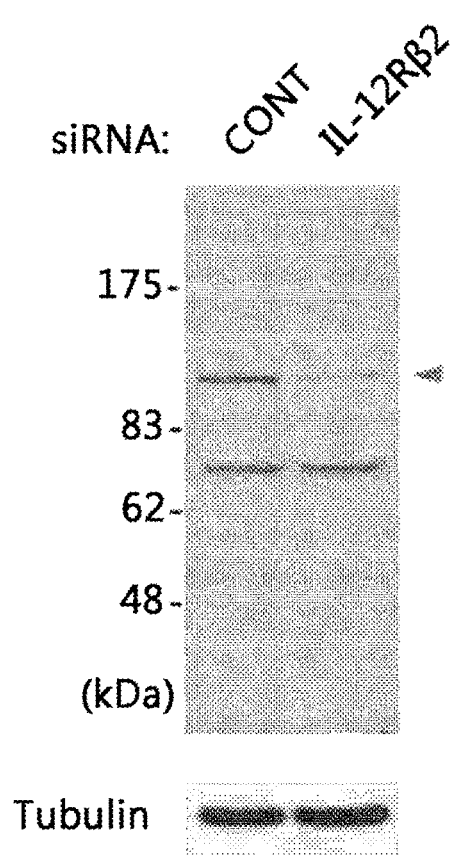
FIG. 6A shows the result of immunoblotting to analyze antigen specificity of anti-IL-1212β2 antibody used in the present invention using IL-1212β2 protein endogenously expressed in U937 cell line.
Figure 6B:
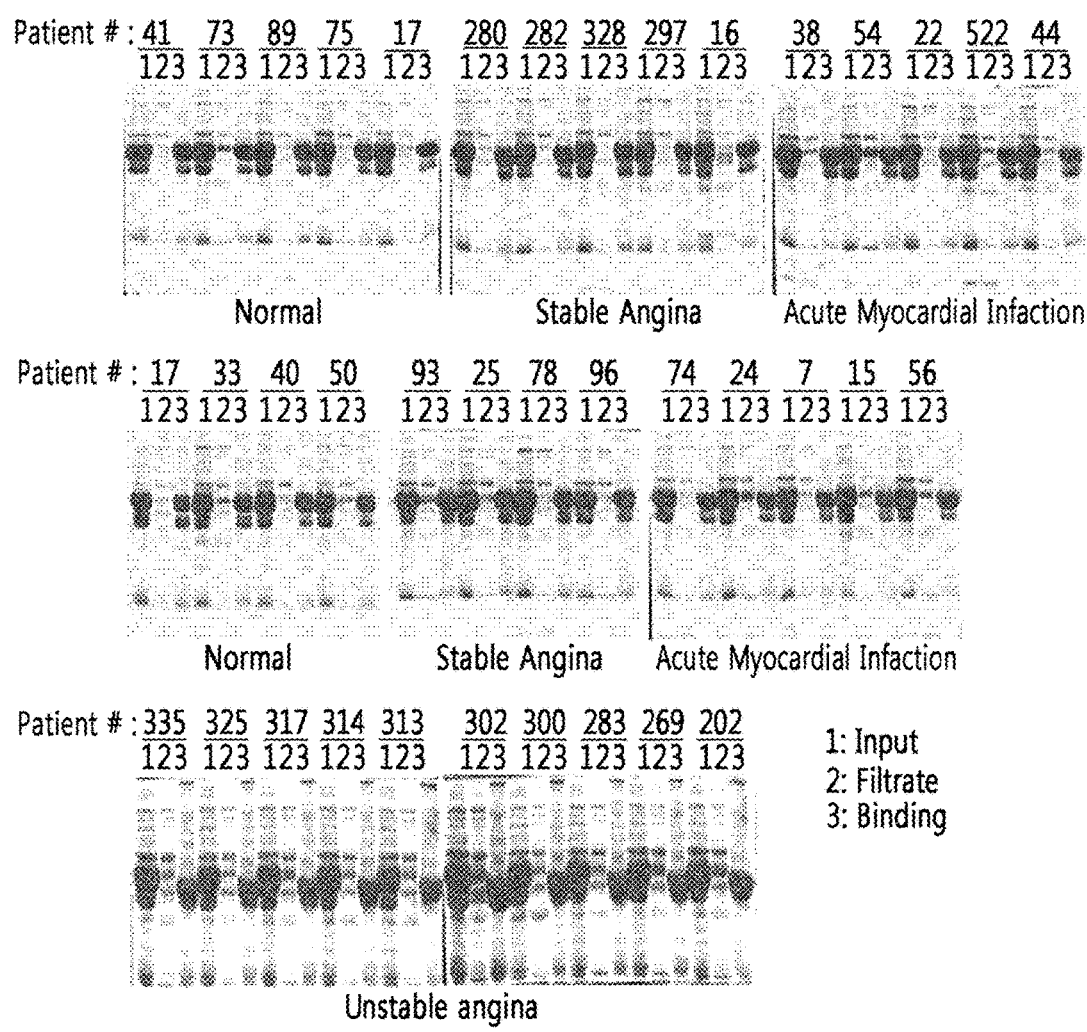
FIG. 6B shows elimination of abundant plasma proteins including albumin and immunoglobulins from the patient plasma samples using a Pierce albumin/IgG removal kit in order to enhance the detection of low-abundance proteins, in which the filtrate 2 is a sample used in FIG. 7A, FIG. 7B, and FIG. 7C.

To do so, antibodies (Santa Cruz Biotech. Clone E-20, Catalog # sc-18648; Atlas antibodies. Product # HPA024168) specifically recognizing IL-1212β2 protein endogenously expressed in the cell lines were used (FIG. 6A). In order to enhance the detection of low-abundance proteins, the abundant plasma proteins including albumin and immunoglobulins were eliminated from the patient plasma samples (FIG. 6B).

Western blot analysis of the plasma samples obtained from patients underwent coronary angiography with angina symptom was performed, and compared to the normal samples. As a result, significantly higher expression level of IL-1212β2 protein was observed in the patient samples than in the normal sample (FIG. 7A, FIG. 7B, FIG. 7C).

As shown in FIG. 8A, the quantitative and statistical analysis indicated that the plasma level of IL12-12β2 was strongly correlated with the disease severity in the human patients ($P=3.448 \times 10^{-6}$ between 4 groups).

Figure 8B:
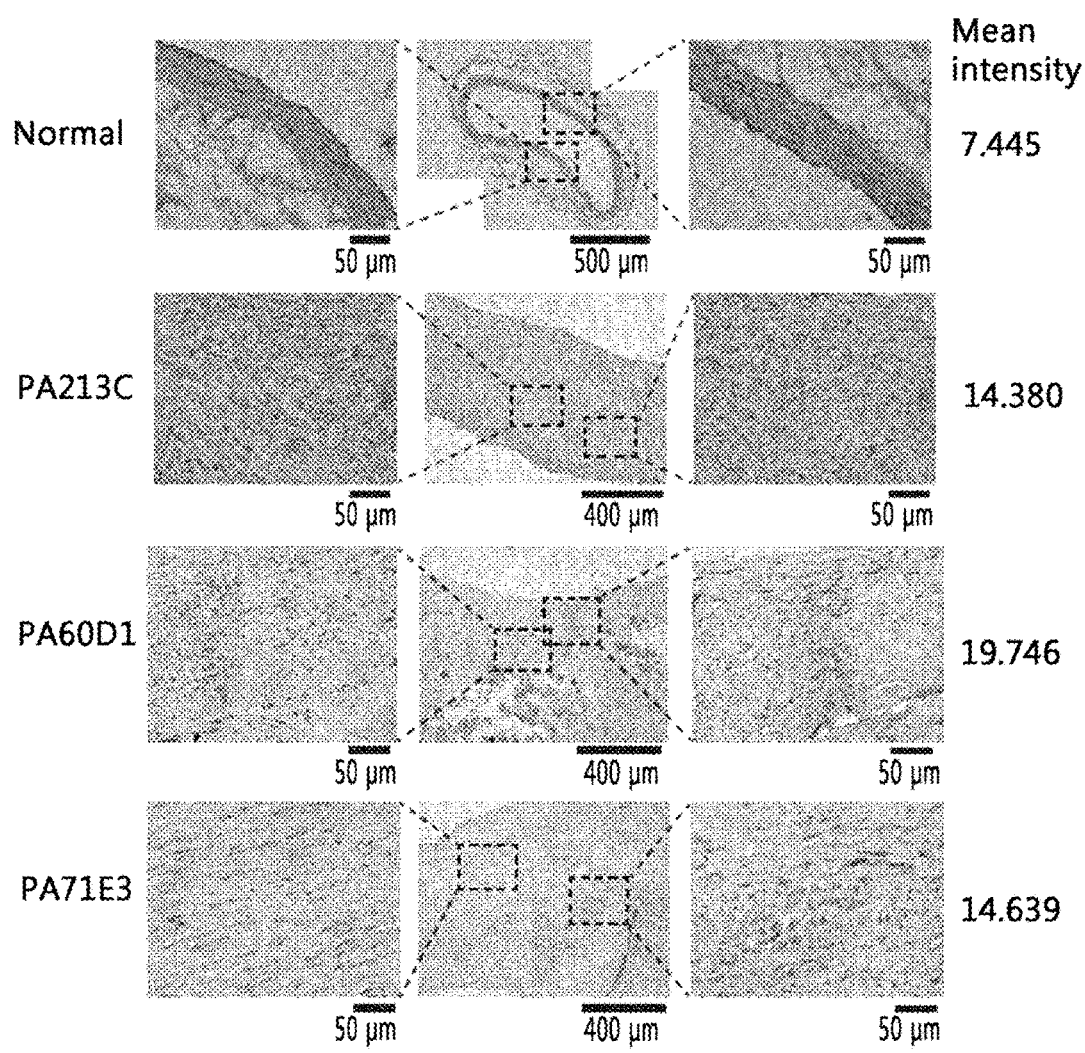
FIG. 8B shows the staining result of IL-1212β2 in the carotid vessels of human patients (n=3) with pathological intimal thickening.

To support that the plasma IL-12β2 is associated with vascular narrowing, the IL-1212β2 expression was examined by tissue staining in the carotid vessels of human patients (n=3) with pathological intimal thickening. As a result, the IL-12βR2 expression was significantly higher in the thickened intimal lesions, compared to that in the normal arterial vessel wall (FIG. 8B).

Since the molecular size of IL-1212β2 detected in the plasma corresponded to the full-length form, it was presumed that IL-1212β2 could be released in the form of extracellular vesicles, not by proteolytic shedding. To confirm this, the present inventors isolated the extracellular vesicles from the plasma samples by ultracentrifugation and polymer-based precipitation. Indeed, IL-1212β2 was present in the precipitates together with extracellular vesicle markers CD9 and CD81 (FIG. 9A and FIG. 9B). With regard to the extracellular vesicle markers, System Biosciences Inc. Cat # EXOAB-CD63A-1 was used as an antibody specifically binding to CD63, System Biosciences Inc. Cat# EXOAB-CD9A-1 was used as an antibody specifically binding to CD9, and System Biosciences Inc. Cat# EXOAB-CD81A-1 was used as an antibody specifically binding to CD81. In addition, PDGFRβ as a smooth muscle marker was also detected in the extracellular vesicle fraction, indicating the presence of smooth muscle cell-derived extracellular vesicles in the patient plasma samples.

Finally, to examine whether IL-1212β2 and PDGFRβ are located in the same extracellular vesicles, PDGFRβ was immunoprecipitated from the patient plasma using an antibody (Santa Cruz Biotech. clone P-20. Catalog # sc-339) specifically binding to PDGFRβ followed by detecting IL-1212β2. As a result, as shown in FIG. 9C, IL-1212β2 was detected in the PDGFRβ immunoprecipitates, confirming co-localization of both proteins in extracellular vesicles derived from smooth muscle cells.

Taken together, it was confirmed that IL-1212β2 expression is induced in the thickening aortic vessels, and IL-1212β2 is released into the blood of patients due to the plaque instability. In the present invention, accordingly, IL-1212β2 was confirmed to be used as a marker for measuring the severity of disease in terms of the vascular diseases.

Experimental Example 4: IL-12Rβ2 as Potential Biomarker for Vascular Thickening 2

Carotid arteries were removed from a 8-week-old Sprague Dawley male rat and washed with basal DMEM. The arteries were chopped in a few drops of basal DMEM and incubated with 5 mL DMEM supplemented with collagenase (1 mg/mL) and elastase (0.5 mg/mL) for 30 min at 37° C. The digestion step was repeated twice and the cluster of vascular cells was suspended with complete DMEM to stop the enzyme reaction. The digested vessels were centrifuged at 1,000 g for 3 min, and the pellets were suspended in 10 mL of MACS buffer (phosphate-buffered saline (PBS) containing 2 mM EDTA and 0.5% BSA), and then filtered through a 70-μm cell strainer to remove tissue debris. The isolated cells were collected by centrifugation, re-suspended in 500 mL of MACS buffer with mouse anti-rat CD31 antibody (BD Pharmingen), and incubated at room temperature for 10 min. After incubation, the cells were rinsed twice with MACS buffer by repeating centrifugation and re-suspension. The cells were suspended once more in 80 mL MACS buffer and 20 mL of anti-mouse magnetic beads (Miltenyi Biotec) was added. The mixture was left at 4° C. for 15 min and passed over a magnetic column (Miltenyi Biotec). The unbound cells in flow-through fraction were seeded on 60-mm dish with DMEM. After 6 hrs, the floating cells containing immune cells were washed with PBS and the remaining adhered cells, including mainly SMCs and pericytes, were cultured for additional several days until confluent.

Figure 10:
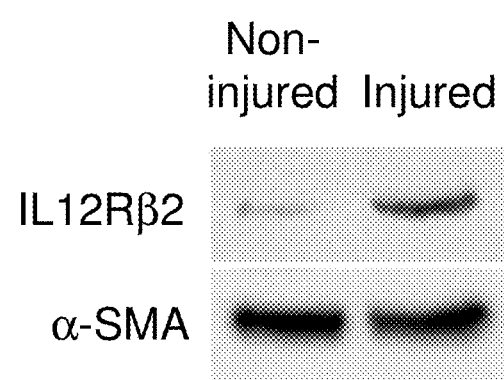
FIG. 10 shows the result of immunoblot analysis for IL-12Rβ2 in the smooth muscle cells isolated from rat carotids without or with balloon injury. Rat carotid vessels were injured by inserting a balloon catheter three times, re-ligated, and then excised after 10 days.

Immunoblot analysis for IL-12Rβ2 in the SMCs isolated from rat carotids with or without balloon injury was carried out, and the result thereof is shown in FIG. 10. As shown in FIG. 10, both samples showed a strong positive response for α-SMA, a marker of vascular smooth muscle cells. However, for IL-12Rβ2, the sample separated from the damaged blood vessels showed a strong positive response, whereas the sample separated from the undamaged blood vessels hardly responded. These results indicate that IL-12Rβ2 can be used as a marker for diagnosing vascular damage.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A method for diagnosing vascular disease, the method comprising the steps of:
(a) collecting an extracellular vesicle derived from smooth muscle cells in a blood sample separated from an individual suspected of having vascular disease;
(b) specifically binding to platelet-derived growth factor receptor-β (PDGFRβ) on the extracellular vesicle with an antibody or aptamer that specifically binds PDGFRβ, thereby isolating the extracellular vesicle;
(c) measuring a level of interleukin 12 receptor β2 protein in the isolated extracellular vesicle; and
(d) comparing the level of interleukin 12 receptor β2 protein measured in step (c) with that in a sample of a normal control group,
wherein if the blood sample of the individual has a higher level of interleukin 12 receptor B2 protein than the sample of the normal control group the individual is diagnosed with vascular disease.

2. The method of claim 1, wherein the method further comprises measuring a level of the extracellular vesicle derived from smooth muscle cells obtained from step (a) using an antibody or an aptamer specific to an extracellular vesicle marker.

3. The method of claim 2, wherein the extracellular vesicle marker is CD81, CD9 or CD63.

4. The method of claim 1, wherein the blood sample of step (a) is a plasma sample.

5. The method of claim 1, wherein the vascular disease is atherosclerosis, in-stent restenosis, myocardial infarction, acute coronary syndrome, or unstable angina.

* * * * *

SEQUENCE LISTING

<160> NUMBER OF SEQ ID NOS: 3

<210> SEQ ID NO 1
<211> LENGTH: 862
<212> TYPE: PRT
<213> ORGANISM: Homo sapiens

<400> SEQUENCE: 1

```
Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
            20                  25                  30

Val Thr Val Lys Pro Ser His Val Ile Leu Leu Gly Ser Thr Val Asn
        35                  40                  45

Ile Thr Cys Ser Leu Lys Pro Arg Gln Gly Cys Phe His Tyr Ser Arg
    50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
            100                 105                 110

Ile Cys Gly Ala Glu Ile Phe Val Gly Val Ala Pro Glu Gln Pro Gln
        115                 120                 125

Asn Leu Ser Cys Ile Gln Lys Gly Glu Gln Gly Thr Val Ala Cys Thr
    130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
        195                 200                 205

Ser Ser Ser Leu Pro Ser Thr Phe Thr Phe Leu Asp Ile Val Arg Pro
    210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
        275                 280                 285

Glu Tyr Glu Phe Gln Ile Ser Ser Lys Leu His Leu Tyr Lys Gly Ser
    290                 295                 300

Trp Ser Asp Trp Ser Glu Ser Leu Arg Ala Gln Thr Pro Glu Glu Glu
305                 310                 315                 320

Pro Thr Gly Met Leu Asp Val Trp Tyr Met Lys Arg His Ile Asp Tyr
                325                 330                 335
```

```
Ser Arg Gln Gln Ile Ser Leu Phe Trp Lys Asn Leu Ser Val Ser Glu
            340                 345                 350

Ala Arg Gly Lys Ile Leu His Tyr Gln Val Thr Leu Gln Glu Leu Thr
            355                 360                 365

Gly Gly Lys Ala Met Thr Gln Asn Ile Thr Gly His Thr Ser Trp Thr
370                 375                 380

Thr Val Ile Pro Arg Thr Gly Asn Trp Ala Val Ala Val Ser Ala Ala
385                 390                 395                 400

Asn Ser Lys Gly Ser Ser Leu Pro Thr Arg Ile Asn Ile Met Asn Leu
                405                 410                 415

Cys Glu Ala Gly Leu Leu Ala Pro Arg Gln Val Ser Ala Asn Ser Glu
            420                 425                 430

Gly Met Asp Asn Ile Leu Val Thr Trp Gln Pro Pro Arg Lys Asp Pro
            435                 440                 445

Ser Ala Val Gln Glu Tyr Val Val Glu Trp Arg Glu Leu His Pro Gly
            450                 455                 460

Gly Asp Thr Gln Val Pro Leu Asn Trp Leu Arg Ser Arg Pro Tyr Asn
465                 470                 475                 480

Val Ser Ala Leu Ile Ser Glu Asn Ile Lys Ser Tyr Ile Cys Tyr Glu
                485                 490                 495

Ile Arg Val Tyr Ala Leu Ser Gly Asp Gln Gly Gly Cys Ser Ser Ile
            500                 505                 510

Leu Gly Asn Ser Lys His Lys Ala Pro Leu Ser Gly Pro His Ile Asn
            515                 520                 525

Ala Ile Thr Glu Glu Lys Gly Ser Ile Leu Ile Ser Trp Asn Ser Ile
            530                 535                 540

Pro Val Gln Glu Gln Met Gly Cys Leu Leu His Tyr Arg Ile Tyr Trp
545                 550                 555                 560

Lys Glu Arg Asp Ser Asn Ser Gln Pro Gln Leu Cys Glu Ile Pro Tyr
                565                 570                 575

Arg Val Ser Gln Asn Ser His Pro Ile Asn Ser Leu Gln Pro Arg Val
            580                 585                 590

Thr Tyr Val Leu Trp Met Thr Ala Leu Thr Ala Ala Gly Glu Ser Ser
            595                 600                 605

His Gly Asn Glu Arg Glu Phe Cys Leu Gln Gly Lys Ala Asn Trp Met
610                 615                 620

Ala Phe Val Ala Pro Ser Ile Cys Ile Ala Ile Met Val Gly Ile
625                 630                 635                 640

Phe Ser Thr His Tyr Phe Gln Gln Lys Val Phe Val Leu Leu Ala Ala
                645                 650                 655

Leu Arg Pro Gln Trp Cys Ser Arg Glu Ile Pro Asp Pro Ala Asn Ser
            660                 665                 670

Thr Cys Ala Lys Lys Tyr Pro Ile Ala Glu Glu Lys Thr Gln Leu Pro
            675                 680                 685

Leu Asp Arg Leu Leu Ile Asp Trp Pro Thr Pro Glu Asp Pro Glu Pro
690                 695                 700

Leu Val Ile Ser Glu Val Leu His Gln Val Thr Pro Val Phe Arg His
705                 710                 715                 720

Pro Pro Cys Ser Asn Trp Pro Gln Arg Glu Lys Gly Ile Gln Gly His
                725                 730                 735

Gln Ala Ser Glu Lys Asp Met Met His Ser Ala Ser Ser Pro Pro Pro
            740                 745                 750
```

| | | | | | | | | | | | | |
|---|---|---|---|---|---|---|---|---|---|---|---|---|
| Pro | Arg | Ala | Leu | Gln | Ala | Glu | Ser | Arg | Gln | Leu | Val | Asp | Leu | Tyr | Lys |
| | | 755 | | | | | 760 | | | | | 765 | | | |

| | | | | | | | | | | | | |
|---|---|---|---|---|---|---|---|---|---|---|---|---|
| Val | Leu | Glu | Ser | Arg | Gly | Ser | Asp | Pro | Lys | Pro | Glu | Asn | Pro | Ala | Cys |
| 770 | | | | | 775 | | | | | 780 | | | | | |

| | | | | | | | | | | | | |
|---|---|---|---|---|---|---|---|---|---|---|---|---|
| Pro | Trp | Thr | Val | Leu | Pro | Ala | Gly | Asp | Leu | Pro | Thr | His | Asp | Gly | Tyr |
| 785 | | | | | 790 | | | | | 795 | | | | | 800 |

| | | | | | | | | | | | | |
|---|---|---|---|---|---|---|---|---|---|---|---|---|
| Leu | Pro | Ser | Asn | Ile | Asp | Asp | Leu | Pro | Ser | His | Glu | Ala | Pro | Leu | Ala |
| | | | 805 | | | | | 810 | | | | | 815 | | |

| | | | | | | | | | | | | |
|---|---|---|---|---|---|---|---|---|---|---|---|---|
| Asp | Ser | Leu | Glu | Glu | Leu | Glu | Pro | Gln | His | Ile | Ser | Leu | Ser | Val | Phe |
| | | | 820 | | | | | 825 | | | | | 830 | | |

| | | | | | | | | | | | | |
|---|---|---|---|---|---|---|---|---|---|---|---|---|
| Pro | Ser | Ser | Ser | Leu | His | Pro | Leu | Thr | Phe | Ser | Cys | Gly | Asp | Lys | Leu |
| | | | | 835 | | | | | 840 | | | | | 845 | |

| | | | | | | | | | | | | |
|---|---|---|---|---|---|---|---|---|---|---|---|---|
| Thr | Leu | Asp | Gln | Leu | Lys | Met | Arg | Cys | Asp | Ser | Leu | Met | Leu |
| 850 | | | | | 855 | | | | | 860 | | | |

<210> SEQ ID NO 2
<211> LENGTH: 4040
<212> TYPE: DNA
<213> ORGANISM: Homo sapiens

<400> SEQUENCE: 2

```
tgcagagaac agagaaagga catctgcgag gaaagttccc tgatggctgt caacaaagtg      60
ccacgtctct atggctgtgt acgctgagca cacgatttta tcgcgcctat catatcttgg     120
tgcataaacg cacctcacct cggtcaaccc ttgctccgtc ttatgagaca ggctttatta     180
tccgcatttt atatgagggg aatctgacgg tggagagaga attatcttgc tcaaggcgac     240
acagcagagc ccacaggtgg cagaatccca cccgagcccg cttcgacccg cggggtggaa     300
accacgggcg cccgcccggc tgcgcttcca gagctgaact gagaagcgag tcctctccgc     360
cctgcggcca ccgcccagcc ccgaccccg ccccggcccg atcctcactc gccgccagct     420
ccccgcgccc accccggagt tggtggcgca gaggcgggag gcggaggcgg agggcgggc     480
gctggcaccg ggaacgcccg agcgccggca gagagcgcgg agagcgcgac acgtgcggcc     540
cagagcaccg ggaccacccg gtccccgcag gcccgggacc gcgcccgctg gcaggcgaca     600
cgtggaagaa tacggagttc tataccagag ttgattgttg atggcacata cttttagagg     660
atgctcattg gcatttatgt ttataatcac gtggctgttg attaaagcaa aaatagatgc     720
gtgcaagaga ggcgatgtga ctgtgaagcc ttcccatgta attttacttg gatccactgt     780
caatattaca tgctctttga agcccagaca aggctgcttt cactattcca gacgtaacaa     840
gttaatcctg tacaagtttg acagaagaat caatttttcac catggccact ccctcaattc     900
tcaagtcaca ggtcttcccc ttggtacaac cttgtttgtc tgcaaactgg cctgtatcaa     960
tagtgatgaa attcaaatat gtggagcaga gatcttcgtt ggtgttgctc cagaacagcc    1020
tcaaaattta tcctgcatac agaagggaga caggggact gtggcctgca cctgggaaag    1080
aggacgagac acccacttat acactgagta tactctacag ctaagtggac caaaaaattt    1140
aacctggcag aagcaatgta aagacattta ttgtgactat ttggactttg aatcaacct    1200
cacccctgaa tcacctgaat ccaatttcac agccaaggtt actgctgtca atagtcttgg    1260
aagctcctct tcacttccat ccacattcac attcttggac atagtgaggc ctcttcctcc    1320
gtgggacatt gaatcaaat ttcaaaaggc ttccgtgagc agatgtaccc tttattggag    1380
agatgaggga ctggtactgc ttaatcgact cagatatcgg cccagtaaca gcaggctctg    1440
gaatatggtt aatgttacaa aggccaaagg aagacatgat ttgctggatc tgaaaccatt    1500
```

```
tacagaatat gaatttcaga tttcctctaa gctacatctt tataagggaa gttggagtga    1560
ttggagtgaa tcattgagag cacaaacacc agaagaagag cctactggga tgttagatgt    1620
ctggtacatg aaacggcaca ttgactacag tagacaacag atttctcttt tctggaagaa    1680
tctgagtgtc tcagaggcaa gaggaaaaat tctccactat caggtgacct tgcaggagct    1740
gacaggaggg aaagccatga cacagaacat cacaggacac acctcctgga ccacagtcat    1800
tcctagaacc ggaaattggg ctgtggctgt gtctgcagca aattcaaaag gcagttctct    1860
gcccactcgt attaacataa tgaacctgtg tgaggcaggg ttgctggctc ctcgccaggt    1920
ctctgcaaac tcagggggca tggacaacat tctggtgact tggcagcctc ccaggaaaga    1980
tccctctgct gttcaggagt acgtggtgga atggagagag ctccatccag ggggtgacac    2040
acaggtccct ctaaactggc tacggagtcg accctacaat gtgtctgctc tgatttcaga    2100
gaacataaaa tcctacatct gttatgaaat ccgtgtgtat gcactctcag gggatcaagg    2160
aggatgcagc tccatcctgg gtaactctaa gcacaaagca ccactgagtg gcccccacat    2220
taatgccatc acagaggaaa aggggagcat tttaatttca tggaacagca ttccagtcca    2280
ggagcaaatg ggctgcctcc tccattatag gatatactgg aaggaacggg actccaactc    2340
ccagcctcag ctctgtgaaa ttccctacag agtctcccaa aattcacatc caataaacag    2400
cctgcagccc cgagtgacat atgtcctgtg gatgacagct ctgacagctg ctggtgaaag    2460
ttcccacgga aatgagaggg aattttgtct gcaaggtaaa gccaattgga tggcgtttgt    2520
ggcaccaagc atttgcattg ctatcatcat ggtgggcatt ttctcaacgc attacttcca    2580
gcaaaaggtg tttgttctcc tagcagccct cagacctcag tggtgtagca gagaaattcc    2640
agatccagca aatagcactt gcgctaagaa atatcccatt gcagaggaga agacacagct    2700
gcccttggac aggctcctga tagactggcc cacgcctgaa gatcctgaac cgctggtcat    2760
cagtgaagtc cttcatcaag tgaccccagt tttcagacat cccccctgct ccaactggcc    2820
acaaagggaa aaaggaatcc aaggtcatca ggcctctgag aaagacatga tgcacagtgc    2880
ctcaagccca ccacctccaa gagctctcca agctgagagc agacaactgg tggatctgta    2940
caaggtgctg gagagcaggg gctccgaccc aaagccagaa aacccagcct gtccctggac    3000
ggtgctccca gcaggtgacc ttcccaccca tgatggctac ttaccctcca acatagatga    3060
cctcccctca catgaggcac ctctcgctga ctctctggaa gaactggagc tcagcacat    3120
ctcccttcct gttttcccct caagttctct tcacccactc accttctcct gtggtgataa    3180
gctgactctg gatcagttaa agatgaggtg tgactccctc atgctctgag tggtgaggct    3240
tcaagcctta aagtcagtgt gccctcaacc agcacagcct gccccaattc ccccagcccc    3300
tgctccagca gctgtcatct ctgggtgcca ccatcggtct ggctgcagct agaggacagg    3360
caagccagct ctgggggagt cttaggaact gggagttggt cttcactcag atgcctcatc    3420
ttgcctttcc cagggcctta aaattacatc cttcactgtg tggacctaga gactccaact    3480
tgaattccta gtaactttct tggtatgctg gccagaaagg gaaatgagga ggagagtaga    3540
aaccacagct cttagtagta atggcataca gtctagagga ccattcatgc aatgactatt    3600
tctaaagcac ctgctacaca gcaggctgta cacagcagat cagtactgtt caacagaact    3660
tcctgagatg atggaaatgt tctacctctg cactcactgt ccagtacatt agacactagg    3720
cacattggct gttaatcact tggaatgtgt ttagcttgac tgaggaatta aattttgatt    3780
gtaaatttaa atcgccacac atggctagtg gctactgtat tggagtgcac agctctagat    3840
ggctcctaga ttattgagag cctccaaaac aaatcaacct agttctatag atgaagacat    3900
```

```
aaaagacact ggtaaacacc aatgtaaaag gccccccaag gtggtcatga ctggtctcat    3960
ttgcagaagt ctaagaatgt acctttttct ggccgggcgt ggtagctcat gcctgtaatc    4020
ccagcacttt gggaggctga                                                4040

<210> SEQ ID NO 3
<211> LENGTH: 2589
<212> TYPE: DNA
<213> ORGANISM: Homo sapiens

<400> SEQUENCE: 3
atggcacata cttttagagg atgctcattg gcatttatgt ttataatcac gtggctgttg      60
attaaagcaa aaatagatgc gtgcaagaga ggcgatgtga ctgtgaagcc ttcccatgta     120
attttacttg gatccactgt caatattaca tgctcttttga agcccagaca aggctgcttt    180
cactattcca gacgtaacaa gttaatcctg tacaagtttg acagaagaat caattttcac    240
catggccact ccctcaattc tcaagtcaca ggtcttcccc ttggtacaac cttgtttgtc    300
tgcaaactgg cctgtatcaa tagtgatgaa attcaaatat gtggagcaga gatcttcgtt    360
ggtgttgctc cagaacagcc tcaaaattta tcctgcatac agaagggaga cagggggact    420
gtggcctgca cctgggaaag aggacgagac acccactat  acactgagta tactctacag    480
ctaagtggac caaaaaattt aacctggcag aagcaatgta agacatttta ttgtgactat    540
ttggactttg gaatcaacct caccccctgaa tcacctgaat ccaatttcac agccaaggtt    600
actgctgtca atagtcttgg aagctcctct tcacttccat ccacattcac attcttggac    660
atagtgaggc ctcttcctcc gtgggacatt agaatcaaat ttcaaaaggc ttccgtgagc    720
agatgtaccc tttattggag agatgaggga ctggtactgc ttaatcgact cagatatcgg    780
cccagtaaca gcaggctctg gaatatggtt aatgttacaa aggccaaagg aagacatgat    840
ttgctggatc tgaaaccatt tacagaatat gaatttcaga tttcctctaa gctacatctt    900
tataagggaa gttggagtga ttggagtgaa tcattgagag cacaaacacc agaagaagag    960
cctactggga tgttagatgt ctggtacatg aaacggcaca ttgactacag tagacaacag   1020
atttctcttt tctggaagaa tctgagtgtc tcagaggcaa gaggaaaaat tctccactat   1080
caggtgacct tgcaggagct gacaggaggg aaagccatga cacagaacat cacaggacac   1140
acctcctgga ccacagtcat tcctagaacc ggaaattggg ctgtggctgt gtctgcagca   1200
aattcaaaag gcagttctct gcccactcgt attaacataa tgaacctgtg tgaggcaggg   1260
ttgctggctc ctcgccaggt ctctgcaaac tcagagggca tggacaacat tctggtgact   1320
tggcagcctc ccaggaaaga tccctctgct gttcaggagt acgtggtgga atggagagag   1380
ctccatccag ggggtgacac acaggtccct ctaaactggc tacggagtcg accctacaat   1440
gtgtctgctc tgatttcaga aacataaaaa tcctacatct gttatgaaat ccgtgtgtat   1500
gcactctcag gggatcaagg aggatgcagc tccatcctgg gtaactctaa gcacaaagca   1560
ccactgagtg gccccacat  taatgccatc acagaggaaa aggggagcat ttaatttca    1620 tggaacagca ttccagtcca ggagcaaatg gctgcctcc  tccattatag gatatactgg   1680
aaggaacggg actccaactc ccagcctcag ctctgtgaaa ttccctacag agtctcccaa   1740
aattcacatc caataaacag cctgcagccc cgagtgacat atgtcctgtg gatgacagct   1800
ctgacagctg ctggtgaaag ttcccacgga aatgagaggg aattttgtct gcaaggtaaa   1860
gccaattgga tggcgtttgt ggcaccaagc atttgcattg ctatcatcat ggtgggcatt   1920
ttctcaacgc attacttcca gcaaaaggtg tttgttctcc tagcagccct cagacctcag   1980
```

-continued

```
tggtgtagca gagaaattcc agatccagca aatagcactt gcgctaagaa atatcccatt    2040
gcagaggaga agacacagct gcccttggac aggctcctga tagactggcc cacgcctgaa    2100
gatcctgaac cgctggtcat cagtgaagtc cttcatcaag tgaccccagt tttcagacat    2160
cccccctgct ccaactggcc acaaagggaa aaaggaatcc aaggtcatca ggcctctgag    2220
aaagacatga tgcacagtgc ctcaagccca ccacctccaa gagctctcca agctgagagc    2280
agacaactgg tggatctgta caaggtgctg gagagcaggg gctccgaccc aaagcccgaa    2340
aacccagcct gtccctggac ggtgctccca gcaggtgacc ttcccaccca tgatggctac    2400
ttaccctcca acatagatga cctcccctca catgaggcac ctctcgctga ctctctggaa    2460
gaactggagc ctcagcacat ctcccttcct gttttcccct caagttctct tcacccactc    2520
accttctcct gtggtgataa gctgactctg gatcagttaa agatgaggtg tgactccctc    2580
atgctctga                                                            2589
```